US009139659B2

(12) United States Patent
Hongo et al.

(10) Patent No.: US 9,139,659 B2
(45) Date of Patent: Sep. 22, 2015

(54) IDIOTYPIC ANTIBODIES AND USES THEREOF

(71) Applicant: Genetech, Inc., South San Francisco, CA (US)

(72) Inventors: Jo-Anne Hongo, South San Francisco, CA (US); Yanhong Li, South San Francisco, CA (US); Luna Liu, South San Francisco, CA (US); John Lowe, South San Francisco, CA (US); Mauricio Maia, South San Francisco, CA (US); Rajesh Vij, South San Francisco, CA (US); Terence Wong, South San Francisco, CA (US); Keyang Xu, South San Francisco, CA (US)

(73) Assignee: GENENTECH, INC., South San Francisco, CA (US)

( * ) Notice: Subject to any disclaimer, the term of this patent is extended or adjusted under 35 U.S.C. 154(b) by 0 days.

(21) Appl. No.: 13/841,691

(22) Filed: Mar. 15, 2013

(65) Prior Publication Data

US 2013/0266973 A1 Oct. 10, 2013

Related U.S. Application Data

(60) Provisional application No. 61/616,914, filed on Mar. 28, 2012.

(51) Int. Cl.
  *C07K 16/42* (2006.01)
  *C07K 16/08* (2006.01)
  *G01N 33/68* (2006.01)
  *G01N 33/569* (2006.01)

(52) U.S. Cl.
  CPC ...... *C07K 16/4216* (2013.01); *G01N 33/56994* (2013.01); *G01N 33/686* (2013.01); *C07K 16/088* (2013.01); *C07K 2317/92* (2013.01); *G01N 2333/045* (2013.01)

(58) Field of Classification Search
  CPC ............ A61K 39/12; A61K 2039/505; A61K 35/763; A61K 39/395; A61K 2039/6056; C07K 14/045; C07K 16/00; C07K 16/081; C07K 16/085; C07K 16/468
  See application file for complete search history.

(56) References Cited

U.S. PATENT DOCUMENTS

| | | | |
|---|---|---|---|
| 3,645,090 A * | 2/1972 | Mochizuki et al. | 368/32 |
| 3,645,852 A * | 2/1972 | Axen et al. | 435/181 |
| 3,691,016 A * | 9/1972 | Patel | 435/181 |
| 3,720,760 A * | 3/1973 | Bennich et al. | 436/513 |
| 3,940,475 A * | 2/1976 | Gross | 436/518 |
| 3,969,287 A * | 7/1976 | Jaworek et al. | 526/238.1 |
| 4,195,128 A * | 3/1980 | Hildebrand et al. | 435/178 |
| 4,229,537 A | 10/1980 | Hodgins et al. | |
| 4,247,642 A | 1/1981 | Hirohara et al. | |
| 4,330,440 A | 5/1982 | Ayers et al. | |
| 4,376,110 A | 3/1983 | David et al. | |
| 4,737,456 A | 4/1988 | Weng et al. | |
| 4,816,567 A | 3/1989 | Cabilly et al. | |
| 5,648,237 A | 7/1997 | Carter | |
| 5,789,199 A | 8/1998 | Joly et al. | |
| 5,840,523 A | 11/1998 | Simmons et al. | |
| 5,959,177 A | 9/1999 | Hein et al. | |
| 6,020,208 A | 2/2000 | Hutchens et al. | |
| 6,040,498 A | 3/2000 | Stomp et al. | |
| 6,417,429 B1 | 7/2002 | Hein et al. | |
| 6,420,548 B1 | 7/2002 | Vezina et al. | |
| 6,579,719 B1 | 6/2003 | Hutchens et al. | |
| 6,811,689 B2 | 11/2004 | Zhang et al. | |
| 7,125,978 B1 | 10/2006 | Vezina et al. | |
| 7,704,510 B2 * | 4/2010 | Shenk et al. | 424/230.1 |
| 8,173,362 B2 * | 5/2012 | Shenk et al. | 435/5 |
| 2008/0213265 A1 | 9/2008 | Lanzavecchia et al. | |
| 2009/0081230 A1 | 3/2009 | Lanzavecchia et al. | |
| 2010/0040602 A1 | 2/2010 | Funaro et al. | |
| 2012/0082666 A1 * | 4/2012 | Chen et al. | 424/133.1 |
| 2013/0089559 A1 * | 4/2013 | Grawunder et al. | 424/139.1 |
| 2013/0195851 A1 * | 8/2013 | Alavattam et al. | 424/133.1 |

FOREIGN PATENT DOCUMENTS

| | | | | |
|---|---|---|---|---|
| EP | 0119629 A2 * | 9/1984 | | |
| WO | WO 9209690 A2 * | 6/1992 | ............ | C12N 15/00 |
| WO | WO 2005019271 A1 * | 3/2005 | | |
| WO | WO 2012047732 A2 * | 4/2012 | | |

OTHER PUBLICATIONS

Mader A, Kunert R. Humanization strategies for an anti-idiotypic antibody mimicking HIV-1 gp41. Protein Eng Des Sel. Dec. 2010;23(12):947-54. Epub Oct. 30, 2010.*
Ibragimova et al. Biophysical Journal, Oct. 1999, vol. 77, pp. 2191-2198.*
Colman et al. Research in Immunology, 1994, vol. 145, pp. 33-36.*
Rudikoff et al. Proc. Natl. Acad. Sci. USA, 1982 vol. 79, pp. 1979-1983.*
Acland et al., Nature, 1990, vol. 343, pp. 662-665.*
Lin et al., Biochemistry, 1975, vol. 14, pp. 1559-1563.*
Schwartz et al., Proc. Natl. Acad. Sci. USA, vol. 1987; 84:6408-6411.*
Lazar et al., Molecular and Cellular Biology, Mar. 1988, vol. 8, No. 3, pp. 1247-1252.*
Burgess et al., Journal of Cell Biology, Nov. 1990, vol. 111, pp. 2129-2138.*
Boeckh et al. "Randomized, placebo-controlled, double-blind study of a *Cytomegalovirus*-specific monoclonal antibody (MSL-109) for prevention of *Cytomegalovirus* infection after allogeneic hematopoietic stem cell transplantation", Biology of Blood and Marrow Transplantation 7:343-351, 2001.
Borucki et al. "A phase II, double-masked, radomized, placebo-controlled evaluation of a human monoclonal anti-*Cytomegalovirus* antibody (MSL-109) in combination with standard therapy versus standard therapy alone in the treatment of AIDS patients with *Cytomegalovirus* retinitis", Antiviral Research 64:103-111, 2004.
Charlton, K. "Expression and isolation of recombinant antibody fragments in *E. coli*", Methods in Molecular Biol. 248: 245-254: Antibody Engineering: Methods and Protocols Edited by B.K.C. Lo Humana Press, Totowa NJ. 2003.

(Continued)

*Primary Examiner* — Benjamin P Blumel
*Assistant Examiner* — Rachel Gill
(74) *Attorney, Agent, or Firm* — Julie Heider; Christopher De Vry; Arnold & Porter LLP

(57) ABSTRACT

The invention provides anti-idiotypic HCMV antibodies as well as methods of using the same.

21 Claims, 9 Drawing Sheets

(56) References Cited

OTHER PUBLICATIONS

Chowdhury, P.S. "Engineering hot spots for affinity enhancement of antibodies", Methods in Molecular Biology 207: 179-196, 2008.
David et al. "Protein iodination with solid state lactoperoxide", Biochemistry 13(5):1014-1021, 1974.
Ezan et al "Bioanalysis of recombinant proteins and antibodies by mass spectrometry", The Analyst 134(5):825-834, 2009.
Goding, J.W. "Production and application of monoclonal antibodies in cell biology, biochemistry and immunology", pp. 59-103, Academic Press, 1983.
Hoogenboom, H.R. "Overview of antibody phage-display technology and its applications", Methods in Molecular Biology 178:1-37, 2001.
Hunter et al. "Preparation of iodine-13I labelled human growth hormone of high specific activity", Nature 194: 495-496, May 5, 1962.
Keay et al. "Anti-idiotype antibodies that mimic gp86 of human *Cytomegalovirus* inhibit viral fusion but not attachment", J Virology 65(9):5124-5128, Sep. 1991.
Li et al. "Optimization of humanized IgGs in glycoengineered *Pichia pastoris*", Nature Biotechnology 24(2):210-215, Feb. 2006.
Marks et al. "By-passing immunization human antibodies from V-gene libraries displayed on phage", J. Mol. Biol. 222:581-597,1991.
Marks et al. "By-passing immunization: building high affinity human antibodies by chain shuffling", Bio/Technology 10:779-783, Jul. 1992.
Mather, J.P. et al. "Culture of testicular cells in hormone-supplemented serum-free medium", Annals NYAS 383:44-68, 1982.
McCafferty et al. "Phage antibodies: filamentous phage display antibody variable domains",Nature 348: 552-554, Dec. 1990.
Mesmin et al. "Liquid chromatography/tandem mass spectrometry assay for the absolute quantification of the expected circulating apelin peptides in human plasma", Rapid Communications in Mass Spectrometry 24:2875-2884, 2010.
Morris, G. E. "Choosing a method for epitope mapping", Methods in Molecular Biology 66:1-9 Epitope Mapping Protocols Edited G. E. Morris Humana Press Inc. Totowa, NJ 1996.
Nygren, H."Conjugation of horseradish peroxidase to fab fragments with different homobifunctional and heterobifunctional cross-linking reagents", Journal of Histochemistry and Cytochemistry 30(5):407-412, 1982.
Pain et al. "Preparation of protein A-peroxidase monoconjugate using a heterobifunctional reagent and its use in enzyme immunoassays", J. Immunological Methods 40:219-230, 1981.
Pluckthun, A. "Mono and bivalent antibody fragments produced in *Escherichia coli*: engineering, folding and antigen binding", Immunological Reviews 130: 151-188, 1992.
Portolano et al. "Lack of promiscuity in autoantigen-specific H and L chain combinations as revealed by human H and L chain roulette", J. Immunology 150(3):880-887, Feb. 1993.
Rotmans et al. "Cross-linking of *Schistosoma mansoni* antigens and their covalent binding on the surface of polystyrene microtitration trays for use in the ELISA", J. Immunological Methods 57:87-98, 1983.
Tackaberry et al. "Monoclonal anti-idiotypes for the rapid detection of human *Cytomegalovirus*", Journal of Virological Methods 40(2):175-182, Nov. 1992.
Tackaberry et al. "Anti-idiotypic mimicry of a neutralizing epitope on the glycoprotein B complex of human *Cytomegalovirus*", J. Virology 67(11):6815-6819, Nov. 1993.
Winter et al. "Making antibodies by phage display technology", Ann. Rev. Immunol. 12:433-455 , 1994.
Almagro et al. "Humanization of antibodies", Frontier in Bioscience 13:1619-1633, Jan. 1, 2008.
Bass et al. "Hormone Phage: An enrichment method for variant proteins with altered binding properties", Proteins: Structure, Function and Genetics 8: 309-314, 1990.
Boockh et at, "Randomized, placebo-contmlled, double-blind study of a cytomegalovirus-specific monoclonal antibody (MSL-109) for prevention of cytomegalovirus infection after allorneio hematopoietic stem cell transplantation", Biology of Blood and Marrow, Transplantation 7:343-351, 2001.
Borucki et al, "A phase II, double-masked, radomized, placebo-controlled evaluation of a human monoclonal anti-cytortiegalovirus antibody (MSL-109) in combination with standard therapy versus standard therapy alone in the treatment of AIDS patients with cytomegalovirus retinitis", Antiviral Research 64:103-1I1, 2004.
Brodeur, et al. "Mouse-human myeloma partners for the production of heterohybridomas", pp. 51-63 Marcel Dekker, Inc. New York, 1987.
Charlton, "Expression and isolation of recombinant antibody fragments in *E. coli*", Methods in Molecular Biol. 248: 245-254: Antibody Engineering: Methods and Protocols Edited by B.K.C. Lo Humana Press, Totowa NJ, 2003.
Chothia, et al. "Canonical structures for the hypervariable regions of immunoglobulins", J. Mol. Biol. 196: 901-917, 1987.
Chowdhury, P.S. "Engineering hot spots for affinity enhancement: of antibodies", Methods in Molecular Biology 207: 179-196, 2008.
Clackson et al. "Making antibody fragments using phage display libraries", Nature 352: 624-628, Aug. 15, 1991.
Cole, R.B. Ed. Wiley New York, 1997.
Cunningham et al. "High-resolution epitope mapping of Hgh-receptor interactions by alanine-scanning mutagenesis", Science 244: 1081-1085, Jun. 1989.
David at al. "Protein iodination with solid state lactoperoxide", Biochemistry 13(5):1014-1021, 1974.
Drobyski et al. "Phase I study of safety and pharmacokinetics of a human anticytomegalovirus monoclonal antibody in allogeneic bone marrow transplant recipients", Transplantation 51:1190-1196, Jun. 1991.
Dubois et al. "Immunopurification and mass spectrometric quantification of the active form of a chimeric therapeutic antibody in human serum", Analytical Chemistry 80(5):1737-1745, Mar. 2008.
Ezan et al "Bioanalysis of recombinant proteins and antibodies by mass spectrometry", The Analyst 134(5);825-834, 2009.
Flatman et al. "Process analytics for purification of monoclonal antibodies", J. Chromatography B. 848:79-87, 2007.
Gale et al. "Small volume and low flow-rate electrospray ionization mass spectrometry of aqueous", Rapid Communications in Mass Spectrometry 7:1017, 1993.
Gerngross, T.U. "Advances in the production of human therapeutic proteins in yeasts and filamentous fungi", Nature Biotechnology 22(11):1409-1414, Nov. 2004.
Graham et al. "Characteristics of a human cell line transformed by DNA from human adenovirus type 5", J. Gen. Virol. 36:59-72, 1977.
Goding, J.W. "Production and application monoclonal antibodies in cell biology, biochemistry and immunology", pp. 59-103, Academic Press, 1983.
Griffiths et al. "Human anti-self antibodies with high specificity from phage display libraries", EMBO Journal 12(2):725-734, 1993.
Hagman et al. "Absolute quantification of monoclonal antibodies in biofluids by liquid chromatography-tandem mass spectrometry", Analytical Chemistry 80(4): 1290-1296, Feb. 15, 2008.
Harlow and Lane "Antibodies a laboratory Manual", Chapter 3 (Cold Spring Harbor Lab, NY) 1988.
Hoogenboom et al. "By-passing immunisation human antibodies from synthetic repertoires of germline $V_H$ gene segments rearranged in vitro", J. Mol. Biol. 227:381-388, 1992.
Hoogenboom, H.R. "Overview of anitbody phage-display technology and its applications", Methods in Molecular Biology 178:1-37, 2001.
Howard G.C. and Brown W.E. Eds "Modern Protein Chemistry: practical aspects", (2002) CRC Press, Boca Raton, Florida.
Hunter et al. "Preparation of iodine-13I labelled human growth hormone of high specific activity", Nature 194: 495496, May 5,1962.
Kabat et al. Sequences of proteins of itninutiological interest , $5^{th}$ Ed. Public Health Service, National Institutes of Health, Bethesda, MD. vols. 1-3:91/3242,1991.
Keay et al. "Syngeneic monoclonal anti-idiotype antibodies that bear the internal image of a human cytomegalovirus neutralization epitope", J. Immunology 140(3):944-948, Feb. 1988.

(56) References Cited

OTHER PUBLICATIONS

Keay et al. "Anti-idiotype antibodies that mimic gp86 of human cytomegalovirus inhibit viral fusion but not attachment", J Virology 65(9):5121-5128, Sep. 1991.
Kindt et al. Kuby, Immunology 6$^{th}$ Ed. W.H. Freeman and Co. p. 91 (2007).
Kohler et al. "Continous cultures of fused cells secreting antibody of predefined specificity", Nature 256:495-497, Aug. 7, 1975.
Korner et al. "Nano electrospray combined with a quadrupole ion trap for the analysis of peptides and protein digests", Journal of American Society for Mass Spectrometry 7(2):150-156, 1996.
Kozbor et al. "A human hybrid myeloma for production of human monoclonal antibodies", J. Immunology 133:3001-3005, 1984.
Lee, M. "LC/MS applications in drug development" J. Wiley & Sons, New York 2002.
Li et al. "Optimizaticm of humanized IgGs in glycoengineered pichia pastoris", Nature Biotechnology 24(2):210-213, Feb. 2006.
Mann, M and Wilm, M. Anal. Chem. 68:1-8, 1996.
Marks et al. "By-passing immunization human antibodies from V-gene libraries displayed on phage", J. Mol. Biol. 222:381-597, 1991.
Marks et al. "By-passing immunization: building high affinity human antibodies by chain shuffling", Bio/Technology 10;779-783, Jul. 1992.
Mather, J.P. "Establishment and characterization of two distinct mouse testicular epithelial cell lines", Biology of Reproduction 23:243-251, 1980.
Mather, J.P, et al. "Culture of testicular cells in hormone-supplemted serum-free medium", Annals NYAS 383:44-68, 1982.
McCafferty et al. "Phage antibodies: filamentous phage display antibody variable domains", Nature 348: 552-554, Dec. 1990.
Mesmin et al. "MS-based approaches for studying the pharmacokinetics of protein drugs", Bioanalysis 3(5):477-480, 2011.
Mesmin et al. "Liquid chromatography/tandem mass spectrometry assay for the absolute quantification of the expected circulating peptides in human plasma", Rapid Communications in Mass Spectrometry 24:2875-2884, 2010.
Morris, G. E. " Choosing a method for epitope mapping", Methods in Molecular Biology 66:1-9 Epitope Mapping Protocols Edited G. E. Morris Humana Press Inc. Totowa, NJ 1996.
Munson et al. "Ligand: a versatile computerized approach for characterization of ligand-binding systems", Analytical Biochemistry 107:220-239, 1980.
Nigro et al. "Passive immunization during pregnancy for congenital cytomegalovirus infection", New England Journal Medicine 353:1350-1362, 2005.
Nygren, H. "Conjugation of horseradish peroxidase to fab fragments with different homobifunctional and heterobifunctional cross-linking regents", Journal of Hiscochemistry and Cytochemistry 30(5):407-412, 1982.
O'Brien et al. ed., Human Press. Totowa NJ (2001).
O'Sullivan et al. "Methods for the Preparation of enzyme-antibody conjugates for use in enzyme immunoassay", Methods in Enzymology 73:147-166 (Academic Press, New York, NY 1981).
Pain et al. "Preparation of protein A-peroxidase monoconjugate using a heterobifunctional reagent and its use in enzyme immunoassays", J. Immunological Methods 40:219230, 1981.
Pluckthun, A. "Mono and bivalent antibody fragments produced in *escherichia coli*: engineering, folding and antigen binding.", Immunological, Reviews 130: 151-188, 1992.
Portolano et al. "Lack of promiscuity in autoantigen-specific H and L chain combinations as revealed by human H and L chain roulette", J. Immunology 150(3):880-887, Feb 1993.
Rotmans et al. "Cross-linking of schistosorna mansoni antigens and their covalent binding on the surface of polystyrene micotitration trays for use in the ELISA", J. Immunological Methods 57:87-98, 1983.
Skerra et al. "Bacterial expression of immunoglobulin fragments", Current Opinion in Immunology 5:256-262, 1993.
Taekaberry et al. "Monoclonal anti-idiotypes for the rapid detection of human cytomegalovirus", Journal of Virological Methods 40(2):175-182, Nov. 1992.
Tackaberry et al. "Anti-idiotypic mimicry of a neutralizing epitope on the glycoprotein B complex of human cytomegalovirus", J. Virology 67(11):6815-6819, Nov 1993.
Urlaub et al. "Isolation of Chinese hamster cell mutants deficient in dihydrofolate reductase activity", Proc. Natl. Acad. Sci. USA 77(7): 4216-4220, Jul. 1980.
Waterhouse et al. "Combinatorial infection and in vivo recombination: a strategy for making large phage antibody repertoires", Nucleic Acids Research 21(9):2265-2266, 1993.
Winter et al. "Making antibodies by phage display technology", Ann. Rev. Immunol. 12:433-455, 1994.
Yazaki et al. "Expression of recombinant antibodies in mammalian cell lines", Methods in Molecular Biology, vol. 248 :255-268 edited by B.K.C. Lo Humana Press, Totowa NJ, 2003.

\* cited by examiner

Heavy chain: Mouse antibody aligned to mouse germlines

| Kabat number | 1 2 3 4 5 6 7 8 9 10 11 12 13 14 15 16 17 18 19 20 21 22 23 24 25 | CDR H1<br>26 27 28 29 30 31 32 33 34 35 A B | 36 37 38 39 40 41 42 43 44 |
|---|---|---|---|
| IGHV1-54*03 | Q V Q L Q Q S G A E L V R P G T S V K V S C K A S | G Y A F T N Y L I E . . | W V K Q R P G Q G |
| MV.8G8.4.25B10.15 | Q V Q L Q Q S G A E L V R P G T S V K V S C K A S | G Y A F T N Y L I E . . | W V K Q R P G Q G |

| Kabat number | 45 46 47 48 49 50 51 52 A B C 53 54 55 56 57 58 59 60 61 62 63 64 65 | 66 67 68 69 70 71 72 73 74 75 76 77 78 79 80 81 82 A B C 83 84 |
|---|---|---|
| | L E W I G | CDR H2<br>V I N P . . G S G G T N Y N E K F K G | K A T L T A D K S S S T A Y M Q L S S L T S |
| IGHV1-54*03 | L E W I G V I N P . . G S G G T N Y N E K F K G | K A T L T A D K S S S T A Y M Q L S S L T S |
| MV.8G8.4.25B10.15 | L E W I G V I N P . . G S G G T N Y N E K F E A | K A T L T A D K S S S T A Y M Q L S S L T S |

| Kabat number | 85 86 87 88 89 90 91 92 93 94 95 96 97 98 | CDR H3<br>99 100 A B 101 102 103 104 105 106 107 108 109 110 111 112 113 | |
|---|---|---|---|
| IGHV1-54*03 | D D S A V Y F C A R . . . . . | Y W Y F D V W G A G T T V T V S S | IGHJ1*01/02 |
| MV.8G8.4.25B10.15 | D D S A V Y F C A R H G S S . | Y W Y F D V W G A G T T V T V S S | |

IGHD: None found

FIG. 1

Light chain, Kappa: Mouse antibody aligned to mouse germlines

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | A | B | C | D | E | F | 28 | 29 | 30 | 31 | 32 | 33 | 34 | 35 | 36 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | | | | | | | | | | | | | | |
| IGKV5-39*01 | D | I | V | M | T | Q | S | P | A | T | L | S | V | T | P | G | D | R | V | S | L | S | C | R | A | S | Q | . | . | . | . | . | . | S | I | S | D | Y | L | H | W | Y |
| MV.8G8.4.25B10.15 | D | I | V | M | T | Q | S | P | A | T | L | S | V | T | P | G | D | R | V | S | L | S | C | R | A | S | Q | . | . | . | . | . | . | S | I | S | D | Y | L | H | W | Y |

CDR L1: columns 24–36

| Kabat number | 37 | 38 | 39 | 40 | 41 | 42 | 43 | 44 | 45 | 46 | 47 | 48 | 49 | 50 | 51 | 52 | 53 | 54 | A | B | C | D | E | 55 | 56 | 57 | 58 | 59 | 60 | 61 | 62 | 63 | 64 | 65 | 66 | 67 | 68 | 69 | 70 | 71 |
|---|---|---|---|---|---|---|---|---|---|---|---|---|---|---|---|---|---|---|---|---|---|---|---|---|---|---|---|---|---|---|---|---|---|---|---|---|---|---|---|---|
| IGKV5-39*01 | Q | Q | K | S | H | E | S | P | R | L | L | I | K | Y | A | S | Q | S | . | . | . | . | . | I | S | G | I | P | S | R | F | S | G | S | G | S | G | S | D | F |
| MV.8G8.4.25B10.15 | Q | Q | K | S | H | E | S | P | R | L | L | I | K | Y | A | S | Q | S | . | . | . | . | . | I | S | G | I | P | S | R | F | S | G | S | G | S | G | S | D | F |

CDR L2: columns 50–56

| Kabat number | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | A | B | C | D | E | F | 96 | 97 | 98 | 99 | 100 | 101 | 102 | 103 | 104 | 105 | 106 | 107 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGKV5-39*01 | T | L | S | I | N | S | V | E | P | E | D | V | G | V | Y | Y | C | Q | N | G | H | S | F | P | . | . | . | . | . | . | Y | T | F | G | G | G | T | K | L | E | I | K |
| MV.8G8.4.25B10.15 | T | L | S | I | N | S | V | E | P | E | D | V | G | V | Y | Y | C | Q | N | G | H | S | F | P | . | . | . | . | . | . | Y | T | F | G | G | G | T | K | L | E | I | K |

CDR L3: columns 89–97; IGKJ2*01 at right

FIG. 2

Heavy chain: Mouse antibody aligned to mouse germlines

```
Kabat number     1  2  3  4  5  6  7  8  9 10 11 12 13 14 15 16 17 18 19 20 21 22 23 24 25 26 27 28 29 30 31 32 33 34 35 A  B  36 37 38 39 40 41 42 43 44
IGHV1-50*01      Q  V  Q  L  Q  Q  P  G  A  E  L  V  K  P  G  A  S  V  K  L  S  C  K  A  S  G  Y  T  F  T  S  Y  W  M  Q        W  V  K  Q  R  P  G  Q  G
MV.MSL109.1.9E1.1 Q  V  Q  L  Q  Q  S  G  A  E  L  V  M  P  G  A  S  V  K  M  S  C  K  A  S  G  Y  T  F  T  D  Y  W  M  Y        W  V  N  Q  R  P  G  Q  G
                                              CDR H1

Kabat number    45 46 47 48 49 50 51 52  A  B  C 53 54 55 56 57 58 59 60 61 62 63 64 65 66 67 68 69 70 71 72 73 74 75 76 77 78 79 80 81 82  A  B  C 83 84
IGHV1-50*01      L  E  W  I  G  E  I  D  P  .  .  S  D  S  Y  T  N  Y  N  Q  K  F  K  G  K  A  T  L  T  V  D  T  S  S  S  T  A  Y  M  Q  L  S  S  L  T  S
MV.MSL109.1.9E1.1 L  E  W  I  G  A  I  D  T  .  .  S  D  S  Y  T  N  Q  K  F  K  G  K  A  T  L  T  V  D  E  S  S  S  T  A  Y  M  Q  L  N  S  L  T  S
                                  CDR H2

Kabat number    85 86 87 88 89 90 91 92 93 94 95 96 97 98 99 100 A  B  C  D 101 102 103 104 105 106 107 108 109 110 111 112 113
IGHV1-50*01      E  D  S  A  V  Y  Y  C  A  R  .  .  .  .  .  .                        Y  Y  A  M  D  Y  W  G  Q  G  T  S  V  T  V  S  S   IGHJ4*01
MV.MSL109.1.9E1.1 E  D  S  A  V  Y  Y  C  A  R  S  G  F  P  L  F                        Y  Y  P  M  D  Y  W  G  Q  G  T  S  V  T  V  S  S
                                               CDR H3
```

IGHD: None found

FIG. 3

Light chain, Lambda: Mouse antibody aligned to mouse germlines

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | A | B | C | D | E | F | 28 | 29 | 30 | 31 | 32 | 33 | 34 | 35 | 36 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | | | | | | | | | | | | | | |
| IGLV1*01 | Q | A | V | V | T | Q | E | S | A | . | L | T | T | S | P | G | E | T | V | T | L | T | C | R | S | S | T | G | A | V | . | . | . | T | T | S | N | Y | A | N | W | V |
| MV.MSL109.1.9E1.1 | Q | A | V | V | T | Q | E | S | A | . | L | T | T | S | P | G | E | T | V | T | L | T | C | R | S | S | T | G | A | V | . | . | . | T | T | S | N | Y | A | N | W | V |

CDR L1 spans positions 24–34.

| Kabat number | 37 | 38 | 39 | 40 | 41 | 42 | 43 | 44 | 45 | 46 | 47 | 48 | 49 | 50 | 51 | 52 | 53 | 54 | A | B | C | D | E | 55 | 56 | 57 | 58 | 59 | 60 | 61 | 62 | 63 | 64 | 65 | 66 | A | B | 67 | 68 | 69 | 70 | 71 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGLV1*01 | Q | E | K | P | D | H | L | F | T | G | L | I | G | G | T | N | N | R | . | . | . | . | . | A | P | G | V | P | A | R | F | S | G | S | L | . | . | I | G | D | K | A |
| MV.MSL109.1.9E1.1 | Q | E | K | P | D | H | L | F | T | G | L | I | G | G | T | V | N | R | . | . | . | . | . | A | P | G | V | P | A | R | F | S | G | S | L | . | . | I | G | D | K | A |

CDR L2 spans positions 50–56.

| Kabat number | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | A | B | C | D | E | F | 96 | 97 | 98 | 99 | 100 | 101 | 102 | 103 | 104 | 105 | 106 | 107 | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGLV1*01 | A | L | T | I | T | G | A | Q | T | E | D | E | A | I | Y | F | C | A | L | W | Y | S | N | H | F | . | . | . | . | . | W | V | F | G | G | G | T | K | L | T | V | L |
| MV.MSL109.1.9E1.1 | A | L | T | I | T | G | A | Q | T | E | D | E | A | V | Y | F | C | A | L | W | Y | S | N | H | . | . | . | . | . | . | L | V | F | G | G | G | T | K | L | T | V | L |

CDR L3 spans positions 89–97. IGLJ1*01

FIG. 4

SEQUENCE LISTING

```
<160> NUMBER OF SEQ ID NOS: 40

<210> SEQ ID NO 1
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Ile
        35                  40                  45

Gly Trp Ile Asn Thr Tyr Thr Gly Glu Pro Thr Tyr Ala Asp Asp Phe
    50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Trp Tyr Tyr Val Ser Asn Tyr Trp Tyr Phe Asp Val Trp
            100                 105                 110

Gly Gln Gly Thr Leu Val Thr Val Ser Ser
        115                 120

<210> SEQ ID NO 2
<211> LENGTH: 115
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 2

Ser Val Leu Thr Gln Ser Pro Ser Ala Ser Ala Ser Leu Gly Ala Ser
1               5                   10                  15

Val Lys Leu Thr Cys Thr Leu Ser Ser Gln His Ser Thr Tyr Thr Ile
            20                  25                  30

Glu Trp Tyr Gln Gln Pro Gly Lys Gly Pro Arg Tyr Leu Met Lys
        35                  40                  45

Leu Lys Lys Asp Gly Ser His Ser Thr Gly Asp Gly Ile Pro Asp Arg
50                  55                  60

Phe Ser Gly Ser Ser Ser Gly Ala Asp Arg Tyr Leu Thr Ile Ser Asn
65                  70                  75                  80

Leu Gln Ser Glu Asp Glu Ala Asp Tyr Tyr Cys Gly Val Gly Asp Thr
                85                  90                  95

Ile Lys Glu Gln Phe Val Tyr Val Phe Gly Gly Gly Thr Lys Leu Thr
                100                 105                 110

Val Leu Gly
        115

<210> SEQ ID NO 3
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Glu Gln Val Leu Glu Ser Gly Gly Gly Leu Val Lys Pro Gly Gly
1               5                   10                  15

Ser Leu Arg Leu Ser Cys Ala Ala Ser Gly Phe Thr Phe Ser Pro Tyr
            20                  25                  30

Ser Val Phe Trp Val Arg Gln Ala Pro Gly Lys Gly Leu Glu Trp Val
        35                  40                  45

Ser Ser Ile Asn Ser Asn Ser Arg Tyr Lys Tyr Tyr Ala Asp Ser Val
50                  55                  60

Lys Gly Arg Phe Thr Ile Ser Arg Asp Asn Ala Glu Asn Ser Ile Phe
65                  70                  75                  80

Leu Gln Met Asn Ser Leu Arg Ala Glu Asp Thr Ala Val Tyr Tyr Cys
                85                  90                  95

Ala Arg Asp Arg Ser Tyr Tyr Ala Phe Ser Ser Gly Ser Leu Ser Asp
                100                 105                 110

Tyr Tyr Tyr Gly Leu Asp Val Trp Gly Gln Gly Thr Leu Val Thr Val
            115                 120                 125

Ser Ser
    130

<210> SEQ ID NO 4
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Asp Ile Val Met Thr Gln Ser Pro Leu Ser Leu Ser Val Thr Pro Gly
1               5                   10                  15

Glu Pro Ala Ser Ile Ser Cys Arg Ser Ser Gln Ser Leu Leu His Thr
            20                  25                  30

Asn Gly Tyr Asn Tyr Leu Asp Trp Tyr Val Gln Lys Pro Gly Gln Ser
        35                  40                  45

Pro Gln Leu Leu Ile Tyr Leu Ala Ser Asn Arg Ala Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Thr Glu Asp Val Gly Val Tyr Tyr Cys Met Gln Ala
                85                  90                  95

Leu Gln Ile Pro Arg Thr Phe Gly Gln Gly Thr Lys Val Glu Ile Lys
            100                 105                 110
```

<210> SEQ ID NO 5
<211> LENGTH: 119
<212> TYPE: PRT
<213> ORGANISM: Mus musculus

<400> SEQUENCE: 5

```
Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Ile Glu Trp Val Lys Gln Arg Pro Gly Gln Gly Leu Glu Trp Ile
        35                  40                  45

Gly Val Ile Asn Pro Gly Ser Gly Gly Thr Asn Tyr Asn Glu Lys Phe
    50                  55                  60

Glu Ala Lys Ala Thr Leu Thr Ala Asp Lys Ser Ser Ser Thr Ala Tyr
65              70                  75                  80

Met Gln Leu Ser Ser Leu Thr Ser Asp Asp Ser Ala Val Tyr Phe Cys
                85                  90                  95

Ala Arg His Gly Ser Ser Tyr Trp Tyr Phe Asp Val Trp Gly Ala Gly
            100                 105                 110

Thr Thr Val Thr Val Ser Ser
        115
```

<210> SEQ ID NO 6
<211> LENGTH: 115
<212> TYPE: PRT
<213> ORGANISM: Mus musculus

<400> SEQUENCE: 6

```
Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Ile Glu Trp Val Lys Gln Arg Pro Gly Gln Gly Leu Glu Trp Ile
        35                  40                  45

Gly Val Ile Asn Pro Gly Ser Gly Gly Thr Asn Tyr Asn Glu Lys Phe
    50                  55                  60

Lys Gly Lys Ala Thr Leu Thr Ala Asp Lys Ser Ser Ser Thr Ala Tyr
65              70                  75                  80

Met Gln Leu Ser Ser Leu Thr Ser Asp Asp Ser Ala Val Tyr Phe Cys
                85                  90                  95
```

-continued

```
Ala Arg Tyr Trp Tyr Phe Asp Val Trp Gly Ala Gly Thr Thr Val Thr
                100                 105                 110

Val Ser Ser
        115

<210> SEQ ID NO 7
<211> LENGTH: 107
<212> TYPE: PRT
<213> ORGANISM: Mus musculus

<400> SEQUENCE: 7

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Tyr
                85                  90                  95

Thr Phe Gly Gly Gly Thr Lys Leu Glu Ile Lys
            100                 105

<210> SEQ ID NO 8
<211> LENGTH: 107
<212> TYPE: PRT
<213> ORGANISM: Mus musculus

<400> SEQUENCE: 8

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Tyr
                85                  90                  95

Thr Phe Gly Gly Gly Thr Lys Leu Glu Ile Lys
            100                 105

<210> SEQ ID NO 9
<211> LENGTH: 121
<212> TYPE: PRT
<213> ORGANISM: Mus musculus

<400> SEQUENCE: 9

Gln Val Gln Leu Gln Gln Ser Gly Ala Glu Leu Val Met Pro Gly Ala
1               5                   10                  15

Ser Val Lys Met Ser Cys Lys Ala Ser Gly Tyr Thr Phe Thr Asp Tyr
            20                  25                  30
```

```
Trp Met Tyr Trp Val Asn Gln Arg Pro Gly Gln Gly Leu Glu Trp Ile
            35                  40                  45

Gly Ala Ile Asp Thr Ser Asp Ser Tyr Thr Thr Tyr Asn Gln Asn Phe
 50                  55                  60

Lys Gly Lys Ala Thr Leu Thr Val Asp Glu Ser Ser Ser Thr Ala Tyr
 65                  70                  75                  80

Met Gln Leu Asn Ser Leu Thr Ser Glu Asp Ser Ala Val Tyr Tyr Cys
                 85                  90                  95

Ala Arg Ser Gly Phe Pro Leu Phe Tyr Tyr Pro Met Asp Tyr Trp Gly
                100                 105                 110

Gln Gly Thr Ser Val Thr Val Ser Ser
            115                 120
```

<210> SEQ ID NO 10
<211> LENGTH: 115
<212> TYPE: PRT
<213> ORGANISM: Mus musculus

<400> SEQUENCE: 10

```
Gln Val Gln Leu Gln Gln Pro Gly Ala Glu Leu Val Lys Pro Gly Ala
 1               5                  10                  15

Ser Val Lys Leu Ser Cys Lys Ala Ser Gly Tyr Thr Phe Thr Ser Tyr
                 20                  25                  30

Trp Met Gln Trp Val Lys Gln Arg Pro Gly Gln Gly Leu Glu Trp Ile
            35                  40                  45

Gly Glu Ile Asp Pro Ser Asp Ser Tyr Thr Asn Tyr Asn Gln Lys Phe
 50                  55                  60

Lys Gly Lys Ala Thr Leu Thr Val Asp Thr Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Tyr Tyr Ala Met Asp Tyr Trp Gly Gln Gly Thr Ser Val Thr
                100                 105                 110

Val Ser Ser
       115
```

<210> SEQ ID NO 11
<211> LENGTH: 109
<212> TYPE: PRT
<213> ORGANISM: Mus musculus

<400> SEQUENCE: 11

```
Gln Ala Val Val Thr Gln Glu Ser Ala Leu Thr Thr Ser Pro Gly Glu
 1               5                  10                  15

Thr Val Thr Leu Thr Cys Arg Ser Ser Thr Gly Ala Val Thr Thr Ser
                 20                  25                  30

Asn Tyr Ala Asn Trp Val Gln Glu Lys Pro Asp His Leu Phe Thr Gly
            35                  40                  45

Leu Ile Gly Gly Thr Val Asn Arg Ala Pro Gly Val Pro Ala Arg Phe
 50                  55                  60

Ser Gly Ser Leu Ile Gly Asp Lys Ala Ala Leu Thr Ile Thr Gly Ala
 65                  70                  75                  80

Gln Thr Glu Asp Glu Ala Val Tyr Phe Cys Ala Leu Trp Tyr Ser Asn
                 85                  90                  95

His Leu Val Phe Gly Gly Gly Thr Lys Leu Thr Val Leu
                100                 105
```

```
<210> SEQ ID NO 12
<211> LENGTH: 110
<212> TYPE: PRT
<213> ORGANISM: Mus musculus

<400> SEQUENCE: 12

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Phe Trp Val Phe Gly Gly Gly Thr Lys Leu Thr Val Leu
            100                 105                 110

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asn Tyr Leu Ile Glu
1               5

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Val Ile Asn Pro Gly Ser Gly Gly Thr Asn Tyr Asn Glu Lys Phe Glu
1               5                   10                  15

Ala

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

His Gly Ser Ser Tyr Trp Tyr Phe Asp Val
1               5                   10

<210> SEQ ID NO 16
<211> LENGTH: 11
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 16

Arg Ala Ser Gln Ser Ile Ser Asp Tyr Leu His
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Tyr Ala Ser Gln Ser Ile Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Asn Gly His Ser Phe Pro Tyr Thr
1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Tyr Trp Met Tyr
1               5

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Ile Asp Thr Ser Asp Ser Tyr Thr Thr Tyr Asn Gln Asn Phe Lys
1               5                   10                  15

Gly

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Gly Phe Pro Leu Phe Tyr Tyr Pro Met Asp Tyr
1               5                   10
```

<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Ser Ser Thr Gly Ala Val Thr Thr Ser Asn Tyr Ala Asn
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Thr Val Asn Arg Ala Pro
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Leu Trp Tyr Ser Asn His Leu Val
1               5

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Glu Gln Phe Val Tyr Val Phe Gly Gly Gly Thr Lys
1               5                   10

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asp Thr Ser Thr Ser Thr Ala Tyr Leu Glu Leu Ser Ser Leu Arg
1               5                   10                  15

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 27

Gly Leu Glu Trp Val Ser Ser Ile Asn Ser Asn Ser Arg
1               5                   10

<210> SEQ ID NO 28
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Alkylated Cys

<400> SEQUENCE: 28

Leu Ser Cys Ala Ala Ser Gly Phe Thr Phe Ser Pro Tyr Ser Val Phe
1               5                   10                  15

Trp Val Arg

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Tyr Thr Phe Thr Asn Tyr Gly Met Asn
1               5                   10

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Trp Ile Asn Thr Tyr Thr Gly Glu Pro Thr Tyr Ala Asp Asp Phe Lys
1               5                   10                  15

Gly

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ser Trp Tyr Tyr Val Ser Asn Tyr Trp Tyr Phe Asp Val
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 32

Thr Leu Ser Ser Gln His Ser Thr Tyr Thr Ile Glu
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Leu Lys Lys Asp Gly Ser His Ser Thr Gly Asp
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Val Gly Asp Thr Ile Lys Glu Gln Phe Val Tyr Val
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Phe Thr Phe Ser Pro Tyr Ser Val Phe
1               5                   10

<210> SEQ ID NO 36
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ser Ser Ile Asn Ser Asn Ser Arg Tyr Lys Tyr Ala Asp Ser Val
1               5                   10                  15

Lys Gly

<210> SEQ ID NO 37
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ala Arg Asp Arg Ser Tyr Tyr Ala Phe Ser Ser Gly Ser Leu Ser Asp
1               5                   10                  15

Tyr Tyr Tyr Gly Leu Asp Val
            20
```

```
<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Arg Ser Ser Gln Ser Leu Leu His Thr Asn Gly Tyr Asn Tyr Leu Asp
1               5                   10                  15

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Leu Ala Ser Asn Arg Ala Ser
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Met Gln Ala Leu Gln Ile Pro Arg Thr
1               5
```

IDIOTYPIC ANTIBODIES AND USES THEREOF

RELATED APPLICATIONS

This application claims the benefit of U.S. Provisional Application No. 61/616,914 filed Mar. 28, 2012, the contents of which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Mar. 15, 2013, is named GNE-0399R1US_SL.txt and is 20,433 bytes in size.

FIELD OF THE INVENTION

The present invention relates to anti-HCMV idiotypic antibodies and methods of using the same.

BACKGROUND

Human cytomegalovirus (HCMV) is a β-herpesvirus and is also known as human herpesvirus-5 (HHV-5). Other species of cytomegalovirus (CMV) exist which infect additional mammals such as murine CMV (MCMV), guinea pig CMV (GPCMV), simian CMV (SCCMV), rhesus CMV (rhCMV) and chimpanzee CMV (CCMV). HCMV is a common herpesvirus that infects nearly 50% of the U.S. population. For the vast majority of human infected individuals, HCMV infection is asymptomatic. However, in conditions of illness, and immune suppression (e.g., HIV infection, drug-induced immune suppression in transplant patients) HCMV reactivation or primary infection causes a variety of clinical manifestations such as mononucleosis, hepatitis, retinitis, pneumonia, blindness and organ failure. In addition, in the setting of pregnancy, the acquisition of primary CMV infection, though of little consequence to the mother, can have severe clinical consequences in the developing fetus.

Congenital HCMV infection is of particular importance as many children born to mothers infected during pregnancy become infected in utero and suffer devastating clinical disease. In the United States and Europe, 126,000 women have primary HCMV infection during pregnancy and approximately 40,000 of the babies born to these mothers have congenital infection. In the U.S., 1 in 750 children are born with or develop disabilities due to HCMV infection, including: mental retardation, hearing loss, vision loss, organ defects, and growth defects. Congenital HCMV infection is the most common infectious cause of fetal abnormalities. After primary infection of a pregnant woman has occurred, there is currently no approved therapy for the prevention or treatment of fetal infection.

In 2005, Nigro and colleagues published a study in which human CMV hyperimmune globulin (HIG) was administered to expectant mothers with primary HCMV infection (Nigro et al. (2005) *New Engl. J. Med.* 353:1350-1362). In one arm of the study only 1 of the 31 infants born to HCMV-infected mothers were born with disease while 7/14 (50%) of children born to untreated women were born with HCMV disease. Id.

During pregnancy, HCMV can spread from the infected mother to the fetus via the placenta. The placenta, which anchors the fetus to the uterus, contains specialized epithelial cells, stromal fibroblast cells, endothelial cells, and specialized macrophages. The HCMV viral surface contains various viral glycoprotein complexes that have been shown to be required for infection of the specific cell types found in the placenta. A complex of CMV glycoproteins containing gH/gL and UL128, UL130 and UL131 (herein referred to as "Complex I") is specifically required for infection of endothelial cells, epithelial cells and macrophages. A complex of CMV glycoproteins containing gH/gL and g0 (herein referred to as "Complex II") is specifically required for infection of fibroblasts. HIG has been shown to block viral entry into all four of the placental cell types that are susceptible to HCMV infection.

Due to the difficulty of preparing and widely distributing HIG and the reluctance of physicians and the medical community to use human blood products, particularly in pregnant women, it would be most beneficial to create a composition comprising a monoclonal antibody or monoclonal antibodies that could protect fetuses from congenital HCMV infection. No monoclonal antibody composition to date has been developed for the prevention of maternal-fetal transmission of CMV. Lanzavecchia and Macagno have disclosed naturally-occurring antibodies that were isolated from the immortalized B cells of infected patients that bind to a conformational epitope resulting from the combination of UL130 and UL131 or a combination of UL128, UL130 and UL131 that neutralizes CMV transmission (U.S. Patent Publication Nos. 2008/0213265 and 2009/0081230). Shenk and Wang have disclosed antibodies that bind to proteins of Complex I (U.S. Pat. No. 7,704,510). Funaro et al. also disclose neutralizing antibodies to CMV in U.S. Patent Publication No. 2010-0040602. Additionally, an anti-gH monoclonal antibody, MSL-109 was tested in humans in two patient populations, allogenic bone marrow transplant recipients and patients with AIDS and CMV retinitis (Drobyski et al., *Transplantation* 51:1190-1196 (1991); Boeckh et al., *Biol. Blood Marrow Transplant.* 7:343-351 (2001); and Borucki et al., *Antiviral Res.* 64:103-111 (2004) without success.

U.S. application Ser. No. 13/248,998, incorporated by reference herein in its entirety, discloses humanized anti-HCMV monoclonal antibodies. Antibodies disclosed in U.S. application Ser. No. 13/248,998 were shown to have neutralizing potency comparable to human immunoglobulin from patients infected with HCVM (HIG) for inhibiting infection on fibroblasts, epithelial cells, endothelial cells and macrophages. These antibodies are useful, for example, for the prevention, inhibition and/or treatment of HCMV infection, congenital HCMV infection and infection of patients through HCMV-infected transplanted tissues.

There is a need in the art to detect therapeutic humanized monoclonal antibodies to HCMV in biological samples and/or clinical samples without also detecting other antibodies directed or not directed to HCMV (e.g., endogenous immunoglobulins). The invention provides anti-idiotypic antibodies that specifically detect certain anti-HCMV antibodies. These antibodies are useful, for example, in pharmacokinetic (PK) and pharmacodynamic studies and for the quantification and monitoring of therapeutic anti-HCMV antibodies in patients.

SUMMARY

The invention provides isolated anti-idiotypic antibodies which specifically bind to anti-HCMV monoclonal antibodies. In one embodiment, the invention provides an isolated anti-idiotypic antibody that specifically binds to an anti-HCMV antibody comprising the heavy chain sequence of SEQ ID NO: 1 and the light chain sequence of SEQ ID NO: 2 or to an anti-HCMV antibody comprising the heavy chain sequence of SEQ ID NO: 3 and the light chain sequence of SEQ ID NO: 4.

In some embodiments, the anti-idotypic antibody specifically binds to an anti-HCMV antibody comprising the heavy chain sequence of SEQ ID NO: 1 and the light chain sequence of SEQ ID NO: 2. In some embodiments, the anti-idotypic antibody specifically binds to an anti-HCMV antibody comprising all six HVRs from an anti-HCMV antibody comprising the heavy chain sequence of SEQ ID NO: 1 and the light chain sequence of SEQ ID NO: 2. In some embodiments, the anti-idiotypic antibody comprises three heavy chain hypervariable regions (HVR-H1, HVR-H2 and HVR-H3) and three light chain hypervariable regions (HVR-L1, HVR-L2 and HVR-L3), wherein: (a) HVR-H1 comprises the amino acid sequence of SEQ ID NO: 13; (b) HVR-H2 comprises the amino acid sequence of SEQ ID NO: 14; (c) HVR-H3 comprises the amino acid sequence of SEQ ID NO: 15; (d) HVR-L1 comprises the amino acid sequence of SEQ ID NO: 16; (e) HVR-L2 comprises the amino acid sequence of SEQ ID NO: 17; and (f) HVR-L3 comprises the amino acid sequence of SEQ ID NO: 18. In some embodiments, the anti-idiotypic antibody comprises the heavy chain sequence of SEQ ID NO: 5 and the light chain sequence of SEQ ID NO: 7.

In some embodiments, the anti-idiotypic antibody specifically binds to an anti-HCMV antibody comprising the heavy chain sequence of SEQ ID NO: 3 and the light chain sequence of SEQ ID NO: 4. In some embodiments, the anti-idiotypic antibody specifically binds to an anti-HCMV antibody comprising all six HVRs from an anti-HCMV antibody comprising the heavy chain sequence of SEQ ID NO: 3 and the light chain sequence of SEQ ID NO: 4. In some embodiments, the anti-idiotypic antibody comprises three heavy chain hypervariable regions (HVR-H1, HVR-H2 and HVR-H3) and three light chain hypervariable regions (HVR-L1, HVR-L2 and HVR-L3), wherein: (a) HVR-H1 comprises the amino acid sequence of SEQ ID NO: 19; (b) HVR-H2 comprises the amino acid sequence of SEQ ID NO: 20; (c) HVR-H3 comprises the amino acid sequence of SEQ ID NO: 21; (d) HVR-L1 comprises the amino acid sequence of SEQ ID NO: 22; (e) HVR-L2 comprises the amino acid sequence of SEQ ID NO: 23; and (f) HVR-L3 comprises the amino acid sequence of SEQ ID NO: 24. In some embodiments, the anti-idiotypic antibody comprises the heavy chain sequence of SEQ ID NO: 9 and the light chain sequence of SEQ ID NO: 11.

In some embodiments, the anti-idiotypic antibody specifically binds to at least one HVR of an anti-HCMV antibody comprising the heavy chain sequence of SEQ ID NO: 1 and the light chain sequence of SEQ ID NO: 2. In some embodiments, the anti-idiotypic antibody specifically binds to at least one HVR of an anti-HCMV antibody comprising the heavy chain sequence of SEQ ID NO: 3 and the light chain sequence of SEQ ID NO: 4. In some embodiments, the anti-idiotypic antibody specifically binds to HVR-H2 (SEQ ID NO: 36) of an anti-HCMV antibody comprising the heavy chain sequence of SEQ ID NO: 3 and the light chain sequence of SEQ ID NO: 4.

In some embodiments, the anti-idiotypic antibody binds to an epitope comprised within an amino acid amino acid sequence selected from SEQ ID NO: 25, SEQ ID NO: 26, SEQ ID NO: 27 and SEQ ID NO: 28. In some embodiments, the anti-idiotypic antibody binds to an epitope that is comprised within an amino acid amino acid sequence selected from SEQ ID NO: 25 or SEQ ID NO: 26. In some embodiments, the anti-idiotypic antibody binds to an epitope that is comprised within an amino acid amino acid sequence selected from SEQ ID NO: 27 or SEQ ID NO: 28.

In some embodiments, any one of the above anti-idiotypic antibodies is conjugated to a detectable label. In some embodiments, any one of the above anti-idiotypic antibodies is conjugated to biotin.

The invention further provides methods of detection using the anti-idiotypic antibodies of the invention. In one embodiment, the invention provides an enzyme-linked immunosorbent assay (ELISA) method for specifically detecting in a biological sample an antibody of interest comprising (a) contacting and incubating the biological sample with a capture reagent, wherein the capture reagent is the anti-idiotypic antibody of claim 1, so as to bind any of the antibody of interest present in the sample, and (b) contacting the capture reagent, and hence any bound antibody of interest, with a detectable antibody that binds to the antibody of interest, and measuring the level of the antibody of interest bound to the anti-idiotypic antibody using a detection means for the detectable antibody, wherein the antibody of interest is selected from (a) a first anti-HCMV antibody comprising the heavy chain sequence of SEQ ID NO: 1 and the light chain sequence of SEQ ID NO: 2; (b) a second anti-HCMV antibody comprising a heavy chain sequence of SEQ ID NO: 3 and a light chain sequence of SEQ ID NO: 4; and (c) a combination thereof.

In some embodiments of the method, the capture reagent is immobilized to a solid support and the method further comprises the step of separating the biological sample from the immobilized capture reagent bound to any of the antibody of interest present. In some embodiments, the immobilized capture reagent is coated on a microtiter plate. In some embodiments, the immobilized capture reagent is conjugated to biotin and bound to a streptavidin coated microtiter plate.

In some embodiments of the method, the detectable antibody is an antibody from a non-human species that binds to human antibodies. In some embodiments, the detectable antibody is a mouse anti-huIgG Fcγ antibody.

In some embodiments of the method, the detectable antibody is directly detectable. In some embodiments, the detectable antibody is conjugated to horseradish peroxidase. In some embodiments, the detectable antibody is detected by a fluorimetric or calorimetric reagent.

The invention further provides a method for specifically detecting in a biological sample an antibody of interest comprising: (a) contacting and incubating the biological sample with an anti-idiotypic antibody that specifically binds to the antibody of interest; (b) contacting and incubating the sample with immunoaffinity beads that bind to the anti-idiotypic antibody; (c) eluting the antibody of interest; (d) applying the eluted antibody of interest to a separation media to effect separation of more than one sample constituent wherein a separated sample constituent comprises the antibody of interest or a fragment or signature peptide thereof and (e) establishing the mass to charge ratio of one or more separated sample constituents by mass spectrometry, wherein the antibody of interest is selected from (a) a first anti-HCMV antibody comprising the heavy chain sequence of SEQ ID NO: 1 and the light chain sequence of SEQ ID NO: 2; (b) a second anti-HCMV antibody comprising a heavy chain sequence of SEQ ID NO: 3 and a light chain sequence of SEQ ID NO: 4; and (c) a combination thereof.

In some embodiments, the method further comprises treating the biological sample with a protease after incubation with the immunoaffinity beads and prior to or after eluting the antibody of interest. In some embodiments, the protease is trypsin.

In some embodiments of the method, the anti-idiotypic antibody is biotinylated. In some embodiments, the anti-idiotypic antibody binds to streptavidin coated paramagnetic immunoaffinity beads.

In some embodiments of the method, the anti-idiotypic antibodies are bound to the immunoaffinity beads prior to contact and incubation with the biological sample.

In some embodiments of the method, the immunoaffinity bead is a magnetic bead.

In some embodiments of the method, the separation media is a chromatography support.

In various embodiments of any of the methods disclosed above, the antibody of interest is an anti-HCMV antibody comprising the heavy chain sequence of SEQ ID NO: 1 and the light chain sequence of SEQ ID NO: 2 and the anti-idiotypic antibody comprises the heavy chain sequence of SEQ ID NO: 5 and the light chain sequence of SEQ ID NO: 7.

In various embodiments of any of the methods disclosed above, the antibody of interest is an anti-HCMV antibody comprising a heavy chain sequence of SEQ ID NO: 1 and a light chain sequence of SEQ ID NO: 2 and the anti-idiotypic antibody comprises three heavy chain hypervariable regions (HVR-H1, HVR-H2 and HVR-H3) and three light chain hypervariable regions (HVR-L1, HVR-L2 and HVR-L3), wherein: (a) HVR-H1 comprises the amino acid sequence of SEQ ID NO: 13; (b) HVR-H2 comprises the amino acid sequence of SEQ ID NO: 14; (c) HVR-H3 comprises the amino acid sequence of SEQ ID NO: 15; (d) HVR-L1 comprises the amino acid sequence of SEQ ID NO: 16; (e) HVR-L2 comprises the amino acid sequence of SEQ ID NO: 17; and (f) HVR-L3 comprises the amino acid sequence of SEQ ID NO: 18. In some embodiments, the anti-idiotypic antibody comprises the heavy chain sequence of SEQ ID NO: 5 and the light chain sequence of SEQ ID NO: 7.

In various embodiments of any of the methods disclosed above, the antibody of interest is an anti-HCMV antibody comprising a heavy chain sequence of SEQ ID NO: 3 and a light chain sequence of SEQ ID NO: 4 and the anti-idiotypic antibody comprises three heavy chain hypervariable regions (HVR-H1, HVR-H2 and HVR-H3) and three light chain hypervariable regions (HVR-L1, HVR-L2 and HVR-L3), wherein: (a) HVR-H1 comprises the amino acid sequence of SEQ ID NO: 19; (b) HVR-H2 comprises the amino acid sequence of SEQ ID NO: 20; (c) HVR-H3 comprises the amino acid sequence of SEQ ID NO: 21; (d) HVR-L1 comprises the amino acid sequence of SEQ ID NO: 22; (e) HVR-L2 comprises the amino acid sequence of SEQ ID NO: 23; and (f) HVR-L3 comprises the amino acid sequence of SEQ ID NO: 24. In some embodiments, the anti-idiotypic antibody comprises the heavy chain sequence of SEQ ID NO: 9 and the light chain sequence of SEQ ID NO: 11.

In some embodiments of any of the methods disclosed above, the antibody of interest is an anti-HCMV antibody comprising the heavy chain sequence of SEQ ID NO: 1 and the light chain sequence of SEQ ID NO: 2 and the anti-idiotypic antibody binds to at least one HVR of an anti-HCMV antibody comprising the heavy chain sequence of SEQ ID NO: 1 and the light chain sequence of SEQ ID NO: 2.

In some embodiments of any of the methods disclosed above, the antibody of interest is an anti-HCMV antibody comprising the heavy chain sequence of SEQ ID NO: 1 and the light chain sequence of SEQ ID NO: 2 and the anti-idiotypic antibody binds to at least one HVR of an anti-HCMV antibody comprising the heavy chain sequence of SEQ ID NO: 3 and the light chain sequence of SEQ ID NO: 4. In some embodiments, the anti-idiotypic antibody specifically binds to HVR-H2 (SEQ ID NO: 36) of an anti-HCMV antibody comprising the heavy chain sequence of SEQ ID NO: 3 and the light chain sequence of SEQ ID NO: 4.

In some embodiments of any of the methods disclosed above, the antibody of interest is an anti-HCMV antibody comprising the heavy chain sequence of SEQ ID NO: 1 and the light chain sequence of SEQ ID NO: 2 and the anti-idiotypic antibody binds to an epitope on the anti-HCMV antibody that is comprised within an amino acid sequence selected from SEQ ID NO: 25 or SEQ ID NO: 26.

In some embodiments of any of the methods disclosed above, the antibody of interest is an anti-HCMV antibody comprising the heavy chain sequence of SEQ ID NO: 3 and the light chain sequence of SEQ ID NO: 4 and the anti-idiotypic antibody binds to an epitope on the anti-HCMV antibody that is comprised within an amino acid amino acid sequence selected from SEQ ID NO: 27 or SEQ ID NO: 28.

In some embodiments of any of the methods disclosed above, the antibody of interest is a first anti-HCMV antibody comprising the heavy chain sequence of SEQ ID NO: 1 and the light chain sequence of SEQ ID NO: 3 and (b) a second anti-HCMV antibody comprising a heavy chain sequence of SEQ ID NO: 3 and a light chain sequence of SEQ ID NO: 4.

In some embodiments of any of the methods disclosed above, the anti-idiotypic antibody binds to the antibody of interest and not to at least one other anti-HCMV antibody in the sample.

In various embodiments of any of the methods disclosed above, the biological sample is isolated from a human subject. In some embodiments, the human subject has been treated with an anti-HCMV antibody selected from (a) a first anti-HCMV antibody comprising the heavy chain sequence of SEQ ID NO: 1 and the light chain sequence of SEQ ID NO: 2; (b) a second anti-HCMV antibody comprising a heavy chain sequence of SEQ ID NO: 3 and a light chain sequence of SEQ ID NO: 4; and (c) a combination thereof.

In some embodiments of any of the methods disclosed above, the method further comprises using a standard curve to determine the level of the antibody of interest compared to a known level.

In some embodiments of any of the methods disclosed above, the biological sample is blood, plasma or serum. In some embodiments, the sample is serum.

The invention further provides for a kit. In an embodiment, the invention provides an immunoassay kit for specifically detecting in a biological sample an antibody of interest selected from (a) a first anti-HCMV antibody comprising the heavy chain sequence of SEQ ID NO: 1 and the light chain sequence of SEQ ID NO: 2; (b) a second anti-HCMV antibody comprising a heavy chain sequence of SEQ ID NO: 3 and a light chain sequence of SEQ ID NO: 4; and (c) a combination thereof, the kit comprising: (a) a container containing, as a capture reagent, an anti-idiotypic antibody that specifically binds to the antibody of interest; (b) a container containing a detectable antibody that binds to the antibody of interest; and (c) instructions for detecting said antibody of interest. In some embodiments, the kit is useful in an ELISA method for detecting the antibody of interest.

In some embodiments, the kit further comprises a solid support for the capture reagent. In some embodiments, the capture reagent is immobilized on the solid support. In some embodiments, the capture reagent is coated on a microtiter plate.

In various embodiments, the anti-idiotypic antibody is one or more of any of the anti-idiotypic antibodies disclosed above. In some embodiments, the anti-idiotypic antibody is selected from (a) a first anti-idiotypic antibody comprising the heavy chain sequence of SEQ ID NO: 5 and the light chain sequence of SEQ ID NO: 7; (b) a second anti-idiotypic antibody comprising a heavy chain sequence of SEQ ID NO: 9 and a light chain sequence of SEQ ID NO: 11; and (c) a combination thereof.

In some embodiments, the anti-idiotypic antibody specifically binds to an anti-HCMV antibody comprising at least one heavy chain hypervariable region selected from the group consisting of NO: 13-24. In one other embodiment, the antibody comprises three heavy chain hypervariable regions (HVR-H1, HVR-H2 and HVR-H3) and three light chain hypervariable regions (HVR-L1, HVR-L2 and HVR-L3), wherein: (a) HVR-H1 comprises the amino acid sequence of SEQ ID NO: 13; (b) HVR-H2 comprises the amino acid sequence of SEQ ID NO: 14; (c) HVR-H3 comprises the amino acid sequence of SEQ ID NO: 15; (d) HVR-L1 comprises the amino acid sequence of SEQ ID NO: 16; (e) HVR-L2 comprises the amino acid sequence of SEQ ID NO: 17; and (f) HVR-L3 comprises the amino acid sequence of SEQ ID NO: 18. In another embodiment, the antibody comprises three heavy chain hypervariable regions (HVR-H1, HVR-H2 and HVR-H3) and three light chain hypervariable regions (HVR-L1, HVR-L2 and HVR-L3), wherein: (a) HVR-H1 comprises the amino acid sequence of SEQ ID NO: 19; (b) HVR-H2 comprises the amino acid sequence of SEQ ID NO: 20; (c) HVR-H3 comprises the amino acid sequence of SEQ ID NO: 21; (d) HVR-L1 comprises the amino acid sequence of SEQ ID NO: 22; (e) HVR-L2 comprises the amino acid sequence of SEQ ID NO: 23; and (f) HVR-L3 comprises the amino acid sequence of SEQ ID NO: 24.

The invention also provides isolated nucleic acid encoding the anti-idiotypic HCMV antibodies of the invention. The invention also provides host cells comprising the nucleic acid encoding such antibodies. The invention further provides a method of producing an antibody comprising culturing the host cells containing the nucleic acid encoding the antibody so that the antibody is produced. The method may further comprise recovering the antibody from the host cell.

BRIEF DESCRIPTION OF THE FIGURES

FIG. 1 shows an amino acid sequence alignment of the heavy chain variable region (VH) of murine mAb 4.25B10.15 (SEQ ID NO: 5) with the mouse germline heavy chain variable domain region IGHV1-54*03 (SEQ ID NO: 6). The hypervariable regions (HVRs) are boxed. Amino acid residues that differ from the mouse germline sequence are highlighted.

FIG. 2 shows an amino acid sequence alignment of the light chain variable region (VL) of murine mAb 4.25B10.15 (SEQ ID NO: 7) with the mouse germline heavy chain variable domain region IGKV5-39*01 (SEQ ID NO: 8). The amino acids are numbered according to Kabat numbering. The hypervariable regions (HVRs) are boxed.

FIG. 3 shows an amino acid sequence alignment of the heavy chain variable region (VH) of murine mAb 1.9E1.1 (SEQ ID NO: 9) with the mouse germline heavy chain variable domain region IGHV1-50*01 (SEQ ID NO: 10). The hypervariable regions (HVRs) are boxed. Amino acid residues that differ from the mouse germline sequence are highlighted.

FIG. 4 shows an amino acid sequence alignment of the light chain variable region (VL) of murine mAb 1.9E1.1 (SEQ ID NO: 11) with the mouse germline heavy chain variable domain region IGLV1*01 (SEQ ID NO: 12). The amino acids are numbered according to Kabat numbering. The hypervariable regions (HVRs) are boxed. Amino acid residues that differ from the mouse germline sequence are highlighted.

DETAILED DESCRIPTION OF EMBODIMENTS OF THE INVENTION

I. Definitions

Figure 5:
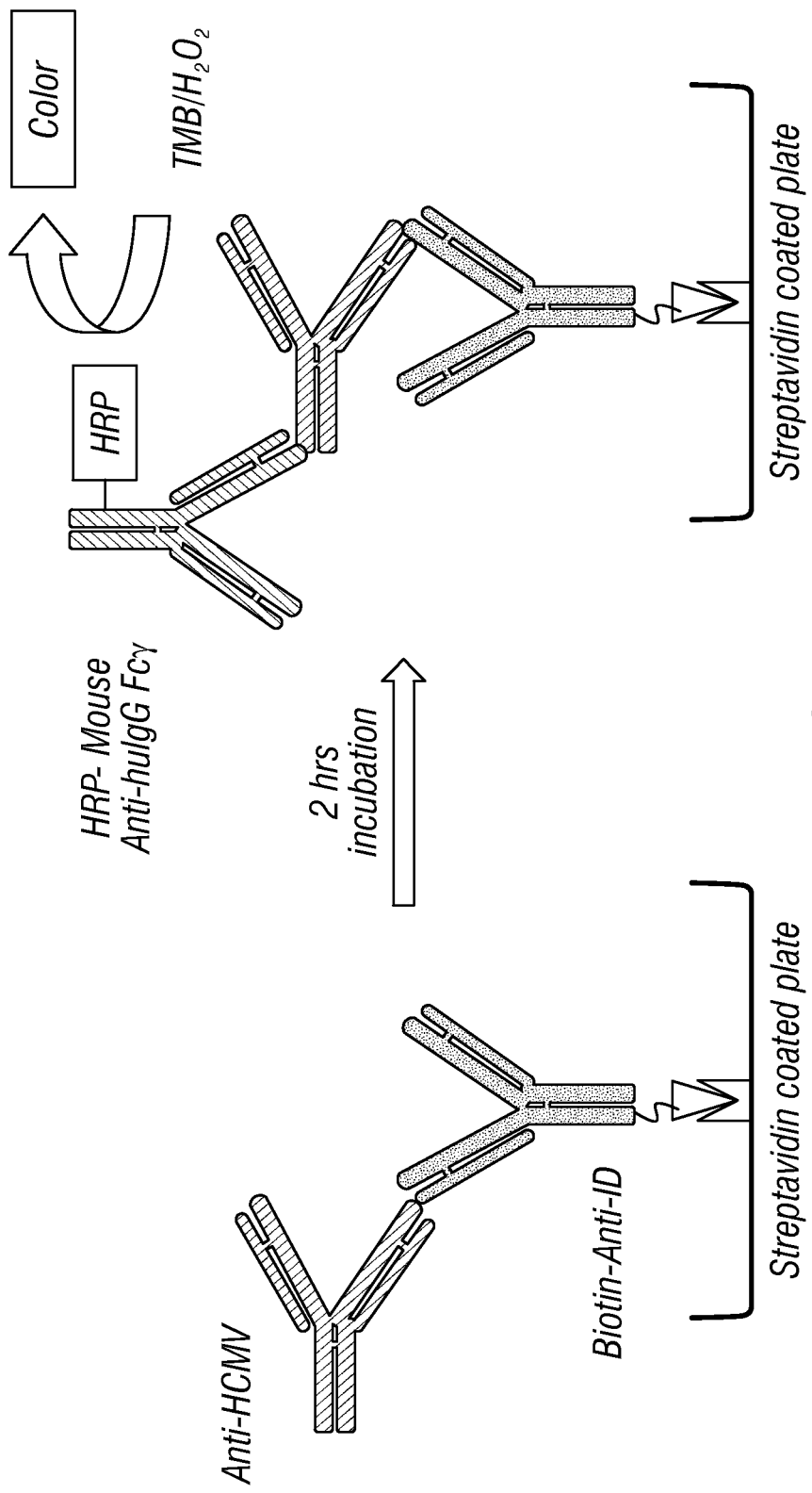
FIG. 5 shows an anti-HCMV PK ELISA format whereby a biotin-conjugated anti-HCMV idiotypic antibody (e.g. 1.9E1.1) binds to a streptavidin coated plate, and to a therapeutic anti-HCMV antibody in solution. The complex is then bound by a mouse anti-human IgG Fcγ antibody conjugated to HRP for chemiluminescent detection.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively. The term "detecting" is used in the broadest sense to include both qualitative and quantitative measurements of a target molecule. In one aspect, the detecting method as described herein is used to identify the mere presence of the antibody of interest in a biological sample. In another aspect, the method is used to test whether the antibody of interest in a sample is present at a detectable level. In yet another aspect, the method can be used to quantify the amount of the antibody of interest in a sample and further to compare the antibody levels from different samples.

The term "biological sample" refers to any biological substance that may contain an antibody of interest. A sample can be biological fluid, such as whole blood or whole blood components including red blood cells, white blood cells, platelets, serum and plasma, ascites, itreous fluid, lymph fluid, synovial fluid, follicular fluid, seminal fluid, amniotic fluid, milk, saliva, sputum, tears, perspiration, mucus, cerebrospinal fluid, and other constituents of the body that may contain the antibody of interest. In various embodiments, the sample is a body sample from any animal. In some embodiments, the sample is from a mammal. In some embodiments, the sample is from a human subject. In some embodiments, the biological sample is from clinical patients or patients treated with a therapeutic anti-HCMV antibody or antibodies.

In certain embodiments, the biological sample is serum or plasma. In certain embodiments, the biological sample is serum from a clinical patient.

The term "capture reagent" or "coat antibody" refers to an anti-idiotypic antibody or mixture of such antibodies that bind an idiotype of the antibody of interest and are capable of binding and capturing the antibody of interest in a biological sample such that under suitable conditions, the complex of capture reagent and antibody of interest can be separated from the rest of the sample.

An "anti-idiotypic antibody," as used herein, is an antibody that binds to the $V_H$ and/or $V_L$ domain of the cognate antibody, in this case the antibody of interest. Typically, such anti-idiotypic antibodies are prepared by immunizing a mammal such as a mouse with the antibody of interest and producing a hybridoma and selecting from the panel of antibodies derived from the hybridoma those antibodies that give the cleanest signal in the assay, whether for the capture reagent or the detectable antibody. Typically, the capture reagent is immobilized or immobilizable. Such anti-idiotypic antibodies are monoclonal antibodies and can be for example, rodent antibodies such as murine or rat antibodies.

The terms "anti-Complex I antibody," "anti-CI antibody" or "anti-CI," as used herein, refers to an anti-HCMV antibody comprising the heavy chain variable domain of SEQ ID NO: 1 and the light chain variable domain of SEQ ID NO: 2 or an antibody comprising at least one HVR region, as shown below:

```
                                                      (SEQ ID NO: 1)
EVQLVQSGAEVKKPGASVKVSCKASGYTFTNYGMNWVRQAPGQGLEWI

GWINTYTGEPTYADDFKGRVTITRDTSTSTAYLELSSLRSEDTAVYYC

ARSWYYVSNYWYFDVWGQGTLVTVSS
The bold, underlined sequences correspond to HVR-H1 (SEQ ID NO: 29), HVR-H2
(SEQ ID NO: 30) and HVR-H3 (SEQ ID NO: 31) of SEQ ID NO: 1.

(SEQ ID NO: 2)
SVLTQSPSASASLGASVKLTCTLSSQHSTYTIEWYQQQPGKGPRYLMK

LKKDGSHSTGDGIPDRFSGSSSGADRYLTISNLQSEDEADYYCGVGDT

IKEQFVYVFGGGTKLTVLG
The bold, underlined sequences correspond to HVR-L1 (SEQ ID NO: 32), HVR-L2
(SEQ ID NO: 33) and HVR-L3 (SEQ ID NO: 34) of SEQ ID NO: 2.
```

The term "anti-gH antibody," or "anti-gH," as used herein, refers to an anti-HCMV antibody comprising the heavy chain variable domain of SEQ ID NO: 3 and the light chain variable domain of SEQ ID NO: 4 or an antibody comprising at least one HVR region, as shown below.

```
                                                      (SEQ ID NO: 3)
EEQVLESGGGLVKPGGSLRLSCAASGFTFSPYSVFWVRQAPGKGLEWV

SSINSNSRYKYYADSVKGRFTISRDNAENSIFLQMNSLRAEDTAVYYC

ARDRSYYAFSSGSLSDYYYGLDVWGQGTLVTVSS
The bold, underlined sequences correspond to HVR-H1 (SEQ ID NO: 35), HVR-H2
(SEQ ID NO: 36) and HVR-H3 (SEQ ID NO: 37) of SEQ ID NO: 3.

(SEQ ID NO: 4)
DIVMTQSPLSLSVTPGEPASISCRSSQSLLHTNGYNYLDWYVQKPGQS

PQLLIYLASNRASGVPDRFSGSGSGTDFTLKISRVETEDVGVYYCMQA

LQIPRTFGQGTKVEIK
The bold, underlined sequences correspond to HVR-L1 (SEQ ID NO: 38), HVR-L2
(SEQ ID NO: 39) and HVR-L3 (SEQ ID NO: 40) of SEQ ID NO: 4.
```

An "anti-CI idiotypic antibody," as used herein, is one that specifically binds to an anti-CI monoclonal antibody having the heavy chain variable domain sequence of SEQ ID NO: 1 and the light chain variable domain sequence of SEQ ID NO: 2, or to an anti-CI antibody comprising all six hypervariable regions of an anti-CI monoclonal antibody having the heavy chain variable domain sequence of SEQ ID NO: 1 and the light chain variable domain sequence of SEQ ID NO: 2 (e.g., SEQ ID NOs: 29-34), with sufficient specificity and affinity to be useful in detection of anti-CI.

An "anti-gH idiotypic antibody," as used herein, is one that specifically binds to an anti-gH monoclonal antibody having the heavy chain variable domain sequence of SEQ ID NO: 3 and the light chain variable domain sequence of SEQ ID NO: 4, or to an anti-gH antibody comprising all six hypervariable regions of an anti-gH monoclonal antibody having the heavy chain variable domain sequence of SEQ ID NO: 3 and the light chain variable domain sequence of SEQ ID NO: 4 (e.g., SEQ ID NOs: 35-40), with sufficient specificity and affinity to be useful in detection of anti-gH.

The term "detectable antibody" refers to an antibody that binds the antibody of interest and is capable of being detected either directly through a label amplified by a detection means, or indirectly through, e.g., another antibody that is labeled. In some embodiments, the detectable antibody is an antibody from a non-human species that binds to human antibodies. In some embodiments, the detectable antibody is an anti-idiotypic antibody or mixture of such antibodies that bind an idiotype of the antibody of interest. For direct labeling, the antibody is typically conjugated to a moiety that is detectable by some means. In some embodiments, the detectable antibody is conjugated to horseradish peroxidase.

The term "detection means" refers to a moiety or technique used to detect the presence of the detectable antibody through signal reporting that is then read out in the assay herein. It includes reagents that amplify the immobilized label such as the label captured onto a microtiter plate.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein. The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest*, 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "infant" as used herein, refers to an individual or subject ranging in age from birth to not more than about one year and includes infants from 0 to about 12 months.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-idiotypic antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

A "signature peptide" of an anti-HCMV antibody refers to a proteolytic peptide (e.g., a tryptic peptide) that is exclusively present in one antibody isotype. For example, an anti-CI signature peptide may be a tryptic peptide that is exclusively present in an anti-HCMV antibody comprising the heavy chain variable domain of SEQ ID NO: 1 and the light chain variable domain of SEQ ID NO: 2. In a further example, an anti-gH signature peptide may be a tryptic peptide that is exclusively present in an antibody an anti-HCMV antibody comprising the heavy chain variable domain of SEQ ID NO: 3 and the light chain variable domain of SEQ ID NO: 4.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Compositions and Methods

In one aspect, the invention provides anti-idiotypic antibodies that specifically bind to the humanized anti-HCMV monoclonal antibodies anti-CI and anti-gH. In certain embodiments, anti-idiotypic antibodies that bind to anti-CI are provided. In certain embodiments, antibodies that bind to anti-gH are provided. Antibodies of the invention are useful, e.g., for the detection and/or quantification of anti-CI and anti-gH in biological samples, for example, in clinical samples.

A. Exemplary Anti-Idiotypic Antibodies

In one aspect, the invention provides isolated anti-idiotypic antibodies that bind to anti-HCMV antibodies anti-CI or anti-gH with sufficient specificity and affinity to be useful in detection of anti-CI and anti-gH.

In certain embodiments, an anti-idiotypic antibody binds to an anti-HCMV antibody comprising the heavy chain sequence of SEQ ID NO: 1 and the light chain sequence of SEQ ID NO: 2. In certain embodiments, an an anti-idiotypic antibody binds to an anti-HCMV antibody comprising all six HVRs from an anti-HCMV antibody comprising the heavy chain sequence of SEQ ID NO: 1 and the light chain sequence of SEQ ID NO: 2. In certain embodiments, an anti-idiotypic antibody binds to an anti-HCMV antibody comprising the heavy chain sequence of SEQ ID NO: 3 and the light chain sequence of SEQ ID NO: 4. In certain embodiments, an an anti-idiotypic antibody binds to an anti-HCMV antibody comprising all six HVRs from an anti-HCMV antibody comprising the heavy chain sequence of SEQ ID NO: 3 and the light chain sequence of SEQ ID NO: 4.

In some embodiments, the anti-idiotypic antibody comprises three heavy chain hypervariable regions (HVR-H1, HVR-H2 and HVR-H3) and three light chain hypervariable regions (HVR-L1, HVR-L2 and HVR-L3), wherein:
 (a) HVR-H1 comprises the amino acid sequence of SEQ ID NO: 13;
 (b) HVR-H2 comprises the amino acid sequence of SEQ ID NO: 14;
 (c) HVR-H3 comprises the amino acid sequence of SEQ ID NO: 15;
 (d) HVR-L1 comprises the amino acid sequence of SEQ ID NO: 16;
 (e) HVR-L2 comprises the amino acid sequence of SEQ ID NO: 17; and
 (f) HVR-L3 comprises the amino acid sequence of SEQ ID NO: 18.

In some embodiments, the anti-idiotypic antibody comprises the heavy chain sequence of SEQ ID NO: 5 and the light chain sequence of SEQ ID NO: 7.

In some embodiments, the anti-idiotypic antibody comprises three heavy chain hypervariable regions (HVR-H1, HVR-H2 and HVR-H3) and three light chain hypervariable regions (HVR-L1, HVR-L2 and HVR-L3), wherein:
 (a) HVR-H1 comprises the amino acid sequence of SEQ ID NO: 19;
 (b) HVR-H2 comprises the amino acid sequence of SEQ ID NO: 20;
 (c) HVR-H3 comprises the amino acid sequence of SEQ ID NO: 21;
 (d) HVR-L1 comprises the amino acid sequence of SEQ ID NO: 22;
 (e) HVR-L2 comprises the amino acid sequence of SEQ ID NO: 23; and
 (f) HVR-L3 comprises the amino acid sequence of SEQ ID NO: 24.

In some embodiments, the anti-idiotypic antibody comprises the heavy chain sequence of SEQ ID NO: 9 and the light chain sequence of SEQ ID NO: 11.

In another aspect, an anti-CI idiotypic antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 5. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-CI idiotypic antibody comprising that sequence retains the ability to bind to anti-CI. In certain embodiments, a total of 1 to 10 amino acids have been substituted, inserted and/or deleted in SEQ ID NO: 5. In certain embodiments, substitutions, insertions, or deletions occur in regions outside the HVRs (i.e., in the FRs). Optionally, the anti-CI idiotypic antibody comprises the VH sequence in SEQ ID NO: 5 including post-translational modifications of that sequence. In a particular embodiment, the VH comprises one, two or three HVRs selected from: (a) HVR-H1 comprising the amino acid sequence of SEQ ID NO: 13, (b) HVR-H2 comprising the amino acid sequence of SEQ ID NO: 14, and (c) HVR-H3 comprising the amino acid sequence of SEQ ID NO: 15

In another aspect, an anti-CI idiotypic antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 7. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-CI idiotypic antibody comprising that sequence retains the ability to bind to anti-CI. In certain embodiments, a total of 1 to 10 amino acids have been substituted, inserted and/or deleted in SEQ ID NO: 7. In certain embodiments, the substitutions, insertions, or deletions occur in regions outside the HVRs (i.e., in the FRs). Optionally, the anti-CI idiotypic antibody comprises the VL sequence in SEQ ID NO: 7, including post-translational modifications of that sequence. In a particular embodiment, the VL comprises one, two or three HVRs selected from (a) HVR-L1 comprising the amino acid sequence of SEQ ID NO: 16; (b) HVR-L2 comprising the amino acid sequence of SEQ ID NO: 17; and (c) HVR-L3 comprising the amino acid sequence of SEQ ID NO: 18.

In another aspect, an anti-CI idiotypic antibody is provided, wherein the antibody comprises a VH as in any of the embodiments provided above, and a VL as in any of the embodiments provided above. In one embodiment, the antibody comprises the VH and VL sequences in SEQ ID NO: 5 and SEQ ID NO: 7, respectively, including post-translational modifications of those sequences.

In another aspect, an anti-gH idiotypic antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 9. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-gH idiotypic antibody comprising that sequence retains the ability to bind to anti-gH. In certain embodiments, a total of 1 to 10 amino acids have been substituted, inserted and/or deleted in SEQ ID NO: 9. In certain embodiments, substitutions, insertions, or deletions occur in regions outside the HVRs (i.e., in the FRs). Optionally, the anti-gH idiotypic antibody comprises the VH sequence in SEQ ID NO: 9 including post-translational modifications of that sequence. In a particular embodiment, the VH comprises one, two or three HVRs selected from: (a) HVR-H1 comprising the amino acid sequence of SEQ ID NO: 19, (b) HVR-H2 comprising the amino acid sequence of SEQ ID NO: 20, and (c) HVR-H3 comprising the amino acid sequence of SEQ ID NO: 21.

In another aspect, an anti-gH idiotypic antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 11. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-gH idiotypic antibody comprising that sequence retains the ability to bind to anti-gH. In certain embodiments, a total of 1 to 10 amino acids have been substituted, inserted and/or deleted in SEQ ID NO: 11. In certain embodiments, the substitutions, insertions, or deletions occur in regions outside the HVRs (i.e., in the FRs). Optionally, the anti-gH idiotypic antibody comprises the VL sequence in SEQ ID NO: 11, including post-translational modifications of that sequence. In a particular embodiment, the VL comprises one, two or three HVRs selected from (a) HVR-L1 comprising the amino acid sequence of SEQ ID NO: 22; (b) HVR-L2 comprising the amino acid sequence of SEQ ID NO: 23; and (c) HVR-L3 comprising the amino acid sequence of SEQ ID NO: 24.

In another aspect, an anti-gH idiotypic antibody is provided, wherein the antibody comprises a VH as in any of the embodiments provided above, and a VL as in any of the embodiments provided above. In one embodiment, the antibody comprises the VH and VL sequences in SEQ ID NO: 9 and SEQ ID NO: 11, respectively, including post-translational modifications of those sequences.

In a further aspect, the invention provides an antibody that binds to the same epitope as an anti-HCMV idiotypic antibody provided herein. For example, in certain embodiments, an antibody is provided that binds to the same epitope as an anti-CI idiotypic antibody comprising a VH sequence of SEQ ID NO: 5 and a VL sequence of SEQ ID NO: 7. in certain embodiments, an antibody is provided that binds to the same epitope as an anti-gH idiotypic antibody comprising a VH sequence of SEQ ID NO: 9 and a VL sequence of SEQ ID NO: 11. In certain embodiments, an antibody is provided that specifically binds to at least one HVR of an anti-HCMV antibody comprising the heavy chain sequence of SEQ ID NO: 1 and the light chain sequence of SEQ ID NO: 2. In certain embodiments, an antibody is provided that specifically binds to at least one HVR of an anti-HCMV antibody comprising the heavy chain sequence of SEQ ID NO: 3 and the light chain sequence of SEQ ID NO: 4. In certain embodiments, an antibody is provided that specifically binds to HVR-H2 (SEQ ID NO: 36) of an anti-HCMV antibody comprising the heavy chain sequence of SEQ ID NO: 3 and the light chain sequence of SEQ ID NO: 4. In certain embodiments, an antibody is provided that binds to an epitope comprised within an amino acid amino acid sequence selected from SEQ ID NO: 25, SEQ ID NO: 26, SEQ ID NO: 27 and SEQ ID NO: 28. In some embodiments, the anti-idiotypic antibody binds to an epitope that is comprised within an amino acid amino acid sequence selected from SEQ ID NO: 25 or SEQ ID NO: 26. In some embodiments, the anti-idiotypic antibody binds to an epitope that is comprised within an amino acid amino acid sequence selected from SEQ ID NO: 27 or SEQ ID NO: 28.

In a further aspect of the invention, an anti-HCMV idiotypic antibody according to any of the above embodiments is a monoclonal antibody, including a chimeric, humanized or human antibody. In one embodiment, an anti-HCMV idiotypic antibody is an antibody fragment, e.g., a Fv, Fab, Fab', scFv, diabody, or F(ab')$_2$ fragment. In another embodiment, the antibody is a full length antibody, e.g., an intact IgG1 antibody or other antibody class or isotype as defined herein.

A. Antibody Production

A description follows as to exemplary techniques for the production of the anti-idiotypic antibodies used in accordance with the present invention.

1. Polyclonal Antibodies

The antibodies of the invention may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include anti-CI, anti-gH, an antigen binding fragment thereof, or fusion proteins thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation. The mammal can then be bled, and the serum assayed for anti-idiotypic antibody titer. If desired, the mammal can be boosted until the antibody titer increases or plateaus.

2. Monoclonal Antibodies

The antibodies of the invention may alternatively be monoclonal antibodies. Monoclonal antibodies may be made using the hybridoma method first described by Kohler et al., *Nature*, 256:495 (1975), or may be made by recombinant DNA methods (see, e/g/ U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium which medium contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Fusion partner myeloma cells are those that fuse efficiently, support stable high-level production of antibody by the selected antibody-producing cells, and are sensitive to a selective medium that selects against the unfused parental cells. Myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection, Manassas, Va., USA. Human myeloma and mouse-human heteromyeloma cell lines also have been described for the production of human monoclonal antibodies (Kozbor, *J. Immunol.*, 133:3001 (1984); and Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. The binding specificity of monoclonal antibodies produced by hybridoma cells may be determined by immunoprecipitation or by an in vitro binding assay, such as radioimmunoassay (RIA) or enzyme-linked immunosorbent assay (ELISA). The binding affinity of the monoclonal antibody can, for example, be determined by the Scatchard analysis described in Munson et al., *Anal. Biochem.*, 107:220 (1980).

Once hybridoma cells that produce antibodies of the desired specificity, affinity, and/or activity are identified, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal e.g., by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Pliickthun, *Immunol. Revs.* 130: 151-188 (1992).

In a further embodiment, monoclonal antibodies or antibody fragments can be isolated from antibody phage libraries generated using the techniques described in McCafferty et al., *Nature*, 348:552-554 (1990). Clackson et al., *Nature*, 352: 624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.* 21:2265-2266 (1993)). Thus, these techniques are viable alternatives to traditional monoclonal antibody hybridoma techniques for isolation of monoclonal antibodies.

In principle, synthetic antibody clones are selected by screening phage libraries containing phage that display various fragments of antibody variable region (Fv) fused to phage coat protein. Such phage libraries are screened for against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution.

Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described in Winter et al., *Ann. Rev. Immunol.*, 12: 433-455 (1994).

Repertoires of VH and VL genes can be separately cloned by polymerase chain reaction (PCR) and recombined randomly in phage libraries, which can then be searched for antigen-binding clones as described in Winter et al., *Ann. Rev. Immunol.*, 12: 433-455 (1994). Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., EMBO J, 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, *J. Mol. Biol.*, 227: 381-388 (1992).

Screening of the libraries can be accomplished by various techniques known in the art. For example, anti-CI or anti-gH can be used to coat the wells of adsorption plates, expressed on host cells affixed to adsorption plates or used in cell sorting, or conjugated to biotin for capture with streptavidin-coated beads, or used in any other method for panning display libraries.

The selection of antibodies with slow dissociation kinetics (and good binding affinities) can be promoted by use of long washes and monovalent phage display as described in Bass et al., *Proteins*, 8: 309-314 (1990) and in WO 92/09690, and a low coating density of antigen as described in Marks et al., *Biotechnol.*, 10: 779-783 (1992).

Any of the anti-idiotypic antibodies of the invention can be obtained by designing a suitable antigen screening procedure to select for the phage clone of interest followed by construction of a full length anti-idiotypic antibody clone using the Fv sequences from the phage clone of interest and suitable constant region (Fc) sequences described in Kabat et al., Sequences of Proteins of Immunological Interest, Fifth Edition, NIH Publication 91-3242, Bethesda Md. (1991), vols. 1-3.

3. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "conservative substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

B. Recombinant Methods and Compositions

Antibodies may be produced using recombinant methods and compositions, e.g., as described in U.S. Pat. No. 4,816,567. In one embodiment, isolated nucleic acid encoding an anti-idiotypic antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-Complex I antibody or anti-gH antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-Complex I antibody or an anti-gH antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology, Vol.* 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977); baby hamster kidney cells (BHK); mouse sertoli cells (TM4 cells as described, e.g., in Mather, *Biol. Reprod.* 23:243-251 (1980); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TR1 cells, as described, e.g., in Mather et al., *Annals N.Y. Acad. Sci.* 383: 44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology, Vol.* 248 (B. K. C. Lo, ed., Humana Press, Totowa, N.J.), pp. 255-268 (2003).

C. Assays

Anti-HCMV idiotypic antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc.

In another aspect, competition assays may be used to identify an antibody that competes for binding of an anti-hCMV antibody with anti-HCMV idiotypic antibodies described herein.

In certain embodiments, such a competing antibody binds to the same epitope (e.g., a linear or a conformational epitope) of anti-CI. In certain embodiments, such a competing antibody binds to the same epitope (e.g., a linear or a conformational epitope) of anti-gH.

Detailed exemplary methods for mapping an epitope to which an antibody binds are provided in Morris (1996) "Epitope Mapping Protocols," in *Methods in Molecular Biology vol.* 66 (Humana Press, Totowa, N.J.).

In an exemplary competition assay, immobilized anti-HCMV antibody is incubated in a solution comprising a first labeled antibody that binds to the anti-HCMV antibody, respectively and a second unlabeled antibody that is being tested for its ability to compete with the first antibody for binding to anti-HCMV antibody. The second antibody may be present in a hybridoma supernatant. As a control, immobilized anti-HCMV antibody is incubated in a solution comprising the first labeled antibody but not the second unlabeled antibody. After incubation under conditions permissive for binding of the first antibody to the anti-HCMV antibody, excess unbound antibody is removed, and the amount of label associated with immobilized anti-HCMV antibody is measured. If the amount of label associated with immobilized anti-HCMV antibody is substantially reduced in the test sample relative to the control sample, then that indicates that the second antibody is competing with the first antibody for binding to anti-HCMV antibody. See Harlow and Lane (1988) *Antibodies: A Laboratory Manual* ch. 14 (Cold Spring Harbor Laboratory, Cold Spring Harbor, N.Y.).

Competition assays can also be performed in a manner as described above with FACS using cells transfected with anti-HCMV antibody and expressed on the cell surface. Additionally, ELISA with anti-HCMV antibody can also be used in a competition assay.

D. Methods and Compositions for Detection

In certain embodiments, any of the anti-idiotypic antibodies, or compositions comprising such antibodies, as provided herein, are useful for detecting the presence of anti-HCMV antibodies anti-CI or anti-gH in a biological sample. The term "detecting" as used herein encompasses quantitative or qualitative detection. In certain embodiments, a biological sample is a biological fluid, such as whole blood or whole blood components including red blood cells, white blood cells, platelets, serum and plasma, ascites, vitreous fluid, lymph fluid, synovial fluid, follicular fluid, seminal fluid, amniotic fluid, milk, saliva, sputum, tears, perspiration, mucus, cerebrospinal fluid, and other constituents of the body that may contain the antibody of interest. In various embodiments, the sample is a body sample from any animal. In some embodiments, the sample is from a mammal. In some embodiments, the sample is from a human subject, for example, when measuring an antibody such as a humanized antibody in a clinical sample. In some embodiments, the biological sample is from clinical patients or a patient treated with a therapeutic anti-HCMV antibody (e.g., anti-CI and/or anti-gH). In certain embodiments, the biological sample is serum or plasma. In certain embodiments, the biological sample is serum from a clinical patient.

In certain embodiments, compositions comprising labeled anti-HCMV idiotypic antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luciferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

1. ELISA

In some embodiments, the anti-HCMV idiotypic antibodies are used in an ELISA assay. The assay described herein is an ELISA that utilizes anti-HCMV idiotypic antibodies as capture reagents for an antibody of interest. In the first step of the assay the biological sample suspected of containing or containing the antibody of interest is contacted and incubated with the capture (or coat) antibodies so that the capture antibodies capture or bind to the antibody of interest so that it can be detected in a detection step. The detection step involves use of a detectable antibody, which, when contacted with any of the bound antibody of interest, binds to the antibody of interest, if present. A detection means is used to detect the label on the antibody and hence the presence or amount of antibody of interest present.

In certain embodiments, the assay utilizes the following steps.

First Step

In the first step of the assay herein, the biological sample suspected of containing or containing the antibody of interest as defined herein is contacted and incubated with the immobilized capture (or coat) reagents, which are anti-idiotypic antibodies directed against the antibody of interest. In some embodiments, these antibodies are monoclonal antibodies, and may be from any species. In some embodiments, the antibodies are rodent antibodies, in further embodiments murine or rat, and in further embodiments murine antibodies.

In various embodiments, the anti-idiotypic is any anti-idiotypic antibody disclosed herein. In certain embodiments, the anti-idiotypic antibody is an antibody comprising three heavy chain hypervariable regions (HVR-H1, HVR-H2 and HVR-H3) and three light chain hypervariable regions (HVR-L1, HVR-L2 and HVR-L3), wherein: (a) HVR-H1 comprises the amino acid sequence of SEQ ID NO: 13; (b) HVR-H2 comprises the amino acid sequence of SEQ ID NO: 14; (c) HVR-H3 comprises the amino acid sequence of SEQ ID NO: 15; (d) HVR-L1 comprises the amino acid sequence of SEQ ID NO: 16; (e) HVR-L2 comprises the amino acid sequence of SEQ ID NO: 17; and (f) HVR-L3 comprises the amino acid sequence of SEQ ID NO: 18. In some embodiments, the anti-idiotypic antibody comprises the heavy chain sequence of SEQ ID NO: 5 and the light chain sequence of SEQ ID NO: 7. In certain embodiments, the anti-idiotypic antibody comprises three heavy chain hypervariable regions (HVR-H1, HVR-H2 and HVR-H3) and three light chain hypervariable regions (HVR-L1, HVR-L2 and HVR-L3), wherein: (a) HVR-H1 comprises the amino acid sequence of SEQ ID NO: 19; (b) HVR-H2 comprises the amino acid sequence of SEQ ID NO: 20; (c) HVR-H3 comprises the amino acid sequence of SEQ ID NO: 21; (d) HVR-L1 comprises the amino acid sequence of SEQ ID NO: 22; (e) HVR-L2 comprises the amino acid sequence of SEQ ID NO: 23; and (f) HVR-L3 comprises the amino acid sequence of SEQ ID NO: 24. In some embodiments, the anti-idiotypic antibody comprises the heavy chain sequence of SEQ ID NO: 9 and the light chain sequence of SEQ ID NO: 11.

Immobilization conventionally is accomplished by insolubilizing the capture reagents either before the assay procedure, as by adsorption to a water-insoluble matrix or surface (U.S. Pat. No. 3,720,760) or non-covalent or covalent coupling (for example, using glutaraldehyde or carbodiimide cross-linking, with or without prior activation of the support with, e.g., nitric acid and a reducing agent as described in U.S. Pat. No. 3,645,852 or in Rotmans et al.; J. Immunol. Methods, 57:87-98 (1983)), or afterward, e.g., by immunoprecipitation. In some embodiments, the capture antibody is conjugated to biotin and is bound to a streptavidin coated surface. In other embodiments, the capture antibody is conjugated to a protein tag, such as a His tag or GST, and is bound to a suitable surface, e.g., a nickel or copper coated surface, or a glutathione coated surface.

The solid phase used for immobilization may be any inert support or carrier that is essentially water insoluble and useful in immunometric assays, including supports in the form of, e.g., surfaces, particles, porous matrices, etc. Examples of commonly used supports include small sheets, SEPHADEX® gels, polyvinyl chloride, plastic beads, and assay plates or test tubes manufactured from polyethylene, polypropylene, polystyrene, and the like, including 96-well microtiter plates, as well as particulate materials such as filter paper, agarose, cross-linked dextran, and other polysaccharides. Alternatively, reactive water-insoluble matrices such as cyanogen-bromide-activated carbohydrates and the reactive substrates described in U.S. Pat. Nos. 3,969,287; 3,691,016; 4,195,128; 4,247,642; 4,229,537; and 4,330,440 are suitably employed for capture-reagent immobilization. In some embodiments, the immobilized capture reagents are coated on a microtiter plate. In some embodiments, the solid phase used is a multi-well microtiter plate that can be used to analyze several samples at one time, for example, a MICROTEST™ or MAXISORP™ 96-well ELISA plate such as that sold as NUNC MAXISORB™ or IMMULONT™.

The solid phase is coated with the capture reagents as defined above, which may be linked by a non-covalent or covalent interaction or physical linkage as desired. Techniques for attachment include those described in U.S. Pat. No. 4,376,110 and the references cited therein. If covalent, the plate or other solid phase is incubated with a cross-linking agent together with the capture reagent under conditions well known in the art such as for one hour at room temperature.

Commonly used cross-linking agents for attaching the capture reagents to the solid-phase substrate include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-((p-azidophenyl)-dithio)propioimidate yield photoactivatable intermediates capable of forming cross-links in the presence of light.

If 96-well plates are utilized, they may be coated with the mixture of capture reagents typically diluted in a buffer such as 0.05 M sodium carbonate by incubation for at least about 10 hours. In some embodiments, incubation is at least overnight, at temperatures of about 4-20° C., or about 4-8° C., and at a pH of about 8-12, about 9-10, or about 9.6. If shorter coating times (1-2 hours) are desired, one can use 96-well plates with nitrocellulose filter bottoms (Millipore MULTI-SCREEN™) or coat at 37° C. The plates may be stacked and coated long in advance of the assay itself, and then the assay can be carried out simultaneously on several samples in a manual, semi-automatic, or automatic fashion, such as by using robotics.

The coated plates are then typically treated with a blocking agent that binds non-specifically to and saturates the binding sites to prevent unwanted binding of the free ligand to the excess sites on the wells of the plate. Examples of appropriate blocking agents for this purpose include, e.g., gelatin, bovine serum albumin, egg albumin, casein, and non-fat milk. The blocking treatment typically takes place under conditions of ambient temperatures for about 1-4 hours, or about 1.5 to 3 hours.

After coating and blocking, the standard (purified antibody of interest) or the biological sample to be analyzed, appropriately diluted, is added to the immobilized phase. In certain embodiments the dilution rate is about 5-15%, or about 10%, by volume. Buffers that may be used for dilution for this purpose include (a) phosphate-buffered saline (PBS) containing 0.5% BSA, 0.05% TWEEN 20™ detergent (P20), 0.05% PROCLIN™ 300 antibiotic, 5 mM EDTA, 0.25% 3-((3-cholamidopropyl)dimethylammonio)-1-propanesulphonate (CHAPS) surfactant, 0.2% beta-gamma globulin, and 0.35M NaCl; (b) PBS containing 0.5% bovine serum albumin (BSA), 0.05% P20, and 0.05% PROCLIN™ 300, pH 7; (c) PBS containing 0.5% BSA, 0.05% P20, 0.05% PROCLIN™ 300, 5 mM EDTA, and 0.35 M NaCl, pH 6.35; (d) PBS containing 0.5% BSA, 0.05% P20, 0.05% PROCLIN™ 300, 5 mM EDTA, 0.2% beta-gamma globulin, and 0.35 M NaCl; and (e) PBS containing 0.5% BSA, 0.05% P20, 0.05% PROCLIN™ 300, 5 mM EDTA, 0.25% CHAPS, and 0.35 M NaCl. PROCLIN™ 300 acts as a preservative, and TWEEN20™ acts as a detergent to eliminate non-specific binding.

The amount of capture reagents employed is sufficiently large to give a good signal in comparison with the standards, but not in molar excess compared to the maximum expected level of antibody of interest in the sample. In certain embodiments, the amount of biological sample added is such that the immobilized capture reagents are in molar excess of the maximum molar concentration of free antibody of interest anticipated in the biological sample after appropriate dilution of the sample. This anticipated level depends mainly on any known correlation between the concentration levels of the free antibody of interest in the particular biological sample being analyzed with the clinical condition of the patient. Thus, for example, an adult patient may have a maximum expected concentration of free antibody of interest in his/her serum that is quite high, whereas a child will be expected to have a lower level of free antibody of interest in his/her serum based on the doses given.

The concentration of the capture reagents may be determined by the concentration range of interest of the antibody of interest, taking any necessary dilution of the biological sample into account. The final concentration of the capture reagents may also be determined empirically to maximize the sensitivity of the assay over the range of interest. Generally, the molar excess is suitably less than about ten-fold of the maximum expected molar concentration of antibody of interest in the biological sample after any appropriate dilution of the sample.

The conditions for incubation of sample and immobilized capture reagent are selected to maximize sensitivity of the assay and to minimize dissociation, and to ensure that any antibody of interest present in the sample binds to the immobilized capture reagent. The incubation is accomplished at fairly constant temperatures, ranging from about 0° C. to about 40° C., for example at or about room temperature. The time for incubation is generally no greater than about 10 hours. In various embodiments, the incubation time is from about 0.5 to 3 hours, or from about 1.5-3 hours at or about room temperature to maximize binding of the antibody of interest to the capture reagents. The duration of incubation may be longer if a protease inhibitor is added to prevent proteases in the biological fluid from degrading the antibody of interest.

At this stage, the pH of the incubation mixture will ordinarily be in the range of about 4-9.5, or in the range of about 6-9, or about 7 to 8. The pH of the incubation buffer is chosen to maintain a significant level of specific binding of the capture reagents to the antibody of interest being captured. Various buffers may be employed to achieve and maintain the desired pH during this step, including borate, phosphate, carbonate, TRIS-HCl or TRIS-phosphate, acetate, barbital, and the like. The particular buffer employed is not critical to the invention, but in individual assays one buffer may be preferred over another.

Optional Second Step

In an optional second step of the assay method, the biological sample is separated (for example by washing) from the immobilized capture reagents to remove uncaptured antibody of interest. The solution used for washing is generally a buffer ("washing buffer") with a pH determined using the considerations and buffers described above for the incubation step, with a pH range of about 6-9. The washing may be done three or more times. The temperature of washing is generally from refrigerator to moderate temperatures, with a constant temperature maintained during the assay period, typically from about 0-40° C., or about 4-30° C. For example, the wash buffer can be placed in ice at 4° C. in a reservoir before the washing, and a plate washer can be utilized for this step. A cross-linking agent or other suitable agent may also be added at this stage to allow the now-bound antibody of interest to be covalently attached to the capture reagents if there is any concern that the captured antibody of interest may dissociate to some extent in the subsequent steps.

Third Step

In the next step, the immobilized capture reagents with any bound antibody of interest present are contacted with detectable antibody at a temperature of about 20-40° C., or about 36-38° C., with the exact temperature and time for contacting the two being dependent primarily on the detection means employed. For example, when 4-methylumbelliferyl-β-galactoside (MUG), streptavidin-HRP, or streptavidin-β-galactosidase is used as the means for detection, the contacting may be carried out overnight (e.g., about 15-17 hours or more) to amplify the signal to the maximum. While the detectable antibody may be a polyclonal or monoclonal antibody, preferably it is a monoclonal antibody, to reduce background noise. In some embodiments, the same anti-idiotypic antibody is used for coat and detection in the assay. In other embodiments, different anti-idiotypic antibodies can be used for coat and detection which are selected so that the background noise is minimized.

In some embodiments, the detectable antibody is an antibody from a non-human species that binds to human antibodies. In some embodiments, the detectable antibody is an anti-huIgG Fc antibody. In some embodiments, the detectable antibody is a mouse anti-huIgG Fcγ antibody. In some embodiments, the detectable antibody is directly detectable. In certain embodiments, the detectable antibody is biotinylated. In such cases, the detection means for the biotinylated label may be avidin or streptavidin-HRP, and the readout of the detection means may be fluorimetric or colorimetric. In some embodiments, the antibody is conjugated to HRP, and the detection means is colorimetric.

A molar excess of detectable antibody with respect to the maximum concentration of free antibody of interest expected (as described above) is added to the plate after it is washed. This antibody (which is directly or indirectly detectable) is a monoclonal antibody, although any antibody can be employed. The affinity of the detectable antibody must be sufficiently high that small amounts of the free antibody of interest can be detected, but not so high that it causes the antibody of interest to be pulled from the capture reagents.

Fourth Step

In the last step of the assay method, the level of any free antibody of interest from the sample that is now bound to the capture reagents is measured using a detection means for the detectable antibody. If the biological sample is from a clinical patient, the measuring step comprises comparing the reaction that occurs as a result of the above three steps with a standard curve to determine the level of antibody of interest compared to the known amount.

The antibody added to the immobilized capture reagents will be either directly labeled, or detected indirectly by addition, after washing off of excess first antibody, of a molar excess of a second, labeled antibody directed against IgG of the animal species of the first antibody. In the latter, indirect assay, labeled antisera against the first antibody are added to the sample so as to produce the labeled antibody in situ.

The label used for either the first or second antibody is any detectable functionality that does not interfere with the binding of free antibody of interest to the anti-idiotypic antibodies. Examples of suitable labels are those numerous labels known for use in immunoassay, including moieties that may be detected directly, such as fluorochrome, chemiluminscent, and radioactive labels, as well as moieties, such as enzymes, that must be reacted or derivatized to be detected. Examples of such labels include the radioisotopes $^{32}P$, $^{14}C$, $^{125}I$, $^{3}H$, and $^{131}I$, fluorophores such as rare-earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, HRP, alkaline phosphatase, .beta.-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin (detectable by, e.g., avidin, streptavidin, streptavidin-HRP, and streptavidin-β-galactosidase with MUG), spin labels, bacteriophage labels, stable free radicals, and the like.

Conventional methods are available to bind these labels covalently to proteins or polypeptides. For instance, coupling agents such as dialdehydes, carbodiimides, dimaleimides, bis-imidates, bis-diazotized benzidine, and the like may be used to tag the antibodies with the above-described fluorescent, chemiluminescent, and enzyme labels. See, for example, U.S. Pat. No. 3,940,475 (fluorimetry) and U.S. Pat. No. 3,645,090 (enzymes); Hunter et al., Nature, 144:945 (1962); David et al., Biochemistry, 13:1014-1021 (1974); Pain et al., J. Immunol. Methods, 40:219-230 (1981); and Nygren, J. Histochem. and Cytochem., 30:407-412 (1982).

The conjugation of such label, including the enzymes, to the antibody is a standard manipulative procedure for one of ordinary skill in immunoassay techniques. See, for example, O'Sullivan et al. "Methods for the Preparation of Enzyme-antibody Conjugates for Use in Enzyme Immunoassay," in Methods in Enzymology, ed. J. J. Langone and H. Van Vunakis, Vol. 73 (Academic Press, New York, N.Y., 1981), pp. 147-166. Suitable commercially available labeled antibodies may also be used.

Following the addition of last labeled antibody, the amount of bound antibody is determined by removing excess unbound labeled antibody through washing and then measuring the amount of the attached label using a detection method appropriate to the label, and correlating the measured amount with the amount of the antibody of interest in the biological sample. For example, in the case of enzymes, the amount of color developed and measured will be a direct measurement of the amount of the antibody of interest present. Specifically, if HRP is the label, the color may be detected using the substrate TMD, using a 450 nm read wavelength and a 620 or 630 nm reference wavelength.

In one example, after an enzyme-labeled second antibody directed against the first unlabeled antibody is washed from the immobilized phase, color or chemiluminiscence is developed and measured by incubating the immobilized capture reagent with a substrate of the enzyme. Then the concentration of the antibody of interest is calculated by comparing with the color or chemiluminescence generated by the standard antibody of interest run in parallel.

2. Mass Spectrometry

In some embodiments, the anti-HCMV idiotypic antibodies are used in a mass spectrometry assay for anti-HCMV antibodies anti-CI and/or anti-gH. The assays described herein utilize anti-HCMV idiotypic antibodies for immunoaffinity capture of anti-HCMV antibodies from a biological sample. The sample may be further processed using a separation technique, such as chromatography, prior to quantification of the anti-HCMV antibodies by mass spectroscopy. In some embodiments, characteristic peptide fragments are produced by proteolysis, and the chosen signature peptides are measured as surrogate analytes for the anti-HCMV antibodies. In certain embodiments, the surrogate peptides are quantified using HPLC with detection by tandem mass spectroscopy (MS/MS).

Processing Biological Samples

An anti-HCMV antibody selected from anti-CI, anti-gH, or a combination thereof is administered to a mammal, such as a human, or contacted with a biological source selected from a tissue, cell culture, plasma or serum. Analysis from serum and plasma samples is known to be problematic due to their high proteomic background, i.e. many proteins and other analytes. After a certain period of time, ranging from minutes, hours, days after administration, a biological sample comprising the anti-HCMV antibody, or fragment thereof is collected. The biological sample may be collected by any means, including withdrawing a fluid by syringe or cannula. The biological sample may be blood or blood products such as serum, plasma or the like or other body fluid containing the antibody of interest.

The biological samples are processed to form analysis samples by conventional procedures including: formulating, immobilizing, centrifugation, isolating, digesting, inducing or preventing blood cell clotting, hydrolyzing, or purifying.

Processing biological samples serves to remove impurities and reduce sample heterogeneity which may hinder separation of the sample constituents, or obscure data collection or analysis. Alternatively, or in addition to, processing simplifies sample handling, preserves from degradation, minimizes sample volume, or selects for the sample constituents (analytes) of interest in the mass spectrometric analysis. Alternatively, or in addition to, processing converts biological samples into metabolites, fragments, or derivatives which are of interest in determining drug metabolism or pharmacokinetic effects.

Capturing Processed Analysis Samples

The antibody is captured on immunoaffinity beads where the beads have an immobilized anti-idiotypic antibody specific for the administered anti-HCMV antibody. In various embodiments, the anti-idiotypic is any anti-idiotypic antibody disclosed herein. The anti-idiotypic antibody specific for the administered anti-HCMV antibody may be conjugated to the immunoaffinity beads using any suitable method known in the art. In some embodiments, the anti-idiotypic specific for the administered anti-HCMV antibody is biotinylated and bound to streptavidin coated paramagnetic beads through strong biotin-streptavidin interaction ($K_D=10^{-15}$ M). Rationales for using streptavidin coated paramagnetic beads include: (i) the strong streptavidin-biotin interaction ($K_D=10^{-15}$ M), (ii) the immobilized streptavidin/biotinylated analyte is a proven method, (iii) the high binding capacity (sufficient material for intact proteins), (iv) low non-specific binding, (v) elution of sample with mass spectrometry-compatible solvents, (vi) good sample recovery from beads, and (vii) ease of use and amenable for automation.

The immunoaffinity bead may comprise a porous polymer monolith and may be configured in a flow-through channel in fluid communication with a collection reservoir. The beads may be contained in a flow-through vessel, such as a column or funnel wherein the sample from the biological source is introduced at one end or orifice, and a sample is eluted from another end or orifice. The immunoaffinity beads may be distributed in a plurality of flow-through vessels, each in communication with a separate collection reservoir. The vessels and reservoirs may be configured in a 96 microtitre well format of 12×8 columns and rows, or a 384 microtitre well format of 24×16 columns and rows for purposes of automation and reproducibility of results.

Plasma or serum samples from the mammal (biological source) that received the anti-HCMV antibody are applied to the beads by manual pipetting or automated robotic dispensing. The beads may be configured in a well or other vessel, or configured in a column, or other flow-through device where the sample is introduced at one end or orifice, and wash effluent or eluted sample is eluted from another end or orifice. Sample constituents specific for the bead bound anti-idiotypic antibody are allowed to bind. The beads are washed to rinse off non-specific proteins and other non-specific sample constituents. Bound antibodies may be deglycosylated on the beads, e.g. with PNGaseF. The bound sample constituents may be eluted into a sample plate, with segregated receiving vessels or wells. The eluted samples may then be addressed by manual pipetting or by robotic transfer and separated by reverse phase chromatography and the separated sample constituents are analyzed by mass spectrometry.

In some embodiments, the biological sample may be digested with a protease. Characteristic peptide fragments are produced by proteolysis, and the chosen signature peptides are measured as surrogate analytes for the anti-HCMV antibodies. In an exemplary embodiment, the biological sample may be digested with trypsin digestion. For trypsin digestion, samples may be reduced with DTT, S-carboxymethylated with sodium iodoacetate, and then digested with trypsin. Digested samples may be analyzed by a separation method, for example, reverse phase HPLC, e.g. Nucleosil C18 column; size-exclusion chromatography (SEC), e.g. TSK 3000SWxL column; or boronate affinity chromatography using a TSK Boronate column.

Separation of Sample Constituents

To form the analysis sample, the biological sample may be applied to a separation media to effect separation of more than one sample constituent. Separation methods include affinity, chromatography, and electrophoresis methods. Affinity methods include affinity chromatography, adsorption, and immobilized affinity matrices. Chromatography methods include HPLC, hydrophobic interaction (HIC), anion exchange, cation exchange, reverse-phase, normal phase, ion-pair reverse-phase, thin-layer, capillary flow, and size-exclusion. Electrophoretic methods include single dimensional, slab gel, capillary, polyacrylamide, denaturing, native, free solution, paper, 2-dimensional, isoelectric focusing, and gradient voltage. Other separation methods include: dialysis, centrifugation, sedimentation, floatation, precipitation, immunoprecipitation, and gel filtration.

Separation methods may effect separation of the constituents of the biological sample by one or more physico-chemical properties including, but not limited to, elution time, hydrophobicity, hydrophilicity, migration time, rate, velocity, chromatographic retention time, solubility, molecular volume or size, net charge, charge state, ionic charge, isoelectric point, dissociation constant (pKa), antibody affinity, electrophoretic mobility, ionization potential, dipole moment, hydrogen-bonding capability, and ion mobility in gas phase.

Low rate of flow by capillary flow infusion into the mass spectrometry inlet device facilitates sensitivity of mass detection, allowing for lower concentration analytes and higher molecular weight species such as intact proteins and antibodies to be detected and characterized.

Mass Spectrometry of Separated Sample Constituents

Preparation of samples for mass spectrometric analysis can be conducted generally according to known techniques. See: "Modern Protein Chemistry: Practical Aspects", Howard, G. C. and Brown, W. E., Eds. (2002) CRC Press, Boca Raton, Fla.

The methods of the invention are appropriate for the analysis of antibody mixtures derived from biological samples where different chemical constituents of the mixture are first isolated, separated, or partially separated by one or more processes including affinity or chromatography which cause the constituents to elute sequentially or in a batch wise manner, or to be directly detected by mass spectrometry. Various structural features and properties of antibodies can be elucidated from mass spectrometry analysis including: fragmentation, deamidation, glycation, oxidation, partial sequence information, e.g. N-terminal and C-terminal, dimer and aggregation states. One or more chemical constituents in the biological sample can be characterized in a highly specific manner by measurement of its accurate mass since the administered anti-HCMV antibody is of known sequence, structure, and molecular weight.

A variety of mass spectrometry systems capable of high mass accuracy, high sensitivity, and high resolution are known in the art and can be employed in the methods of the invention. The mass analyzers of such mass spectrometers include, but are not limited to, quadrupole (Q), time of flight (TOF), ion trap, magnetic sector or FT-ICR or combinations thereof. The ion source of the mass spectrometer should yield mainly sample molecular ions, or pseudo-molecular ions, and certain characterizable fragment ions. Examples of such ion sources include atmospheric pressure ionization sources, e.g. electrospray ionization (ESI) and atmospheric pressure chemical ionization (APCI) and Matrix Assisted Laser Desorption Ionization (MALDI). ESI and MALDI are the two most commonly employed methods to ionize proteins for mass spectrometric analysis. ESI and APCI are the most commonly used ion source techniques for analysis of small molecules by LC/MS (Lee, M. "LC/MS Applications in Drug Development" (2002) J. Wiley & Sons, New York).

Surface Enhanced Laser Desorption Ionization (SELDI) is an example of a surface-based ionization technique that allows for high-throughput mass spectrometry (U.S. Pat. No. 6,020,208). Typically, SELDI is used to analyze complex mixtures of proteins and other biomolecules. SELDI employs a chemically reactive surface such as a "protein chip" to interact with analytes, e.g., proteins, in solution. Such surfaces selectively interact with analytes and immobilize them thereon. Thus, the analytes of the invention can be partially purified on the chip and then quickly analyzed in the mass spectrometer. By providing multiple reactive moieties at different sites on a substrate surface, throughput may be increased.

In functional systems, the mass spectrometer will accurately measure the mass of a chemical species of interest to within 20 ppm of its exact or calculated mass, and typically within 5 ppm or less of its exact or calculated mass. Commercially available mass analyzers can sample and record the whole mass spectrum simultaneously and with a frequency that allows enough spectra to be acquired for a plurality of constituents in the mixture to ensure that the mass spectrometric signal intensity or peak area is quantitatively representative. This will also ensure that the elution times observed for all the masses would not be modified or distorted by the mass analyzer and it would help ensure that quantitative measurements are not compromised by the need to measure abundances of transient signals.

Analytical variability may be corrected for by the use of an internal standard (IS) having physicochemical properties similar to that of the target analyte. (Mesmin et al. (2011) Bioanalysis 3: 477-480). In some embodiments, where signature peptides are measured as surrogate analytes for the anti-HCMV antibodies, stable isotope labled (SIL) peptides corresponding to the signature peptides may be used as internal standards. (Hagman et al. (2008) Anal. Chem. 80: 1290-1296; Mesmin et al. (2010) Rapid Commun. Mass Spectrom. 24: 2875-2884).

Electrospray Ionization Mass Spectrometry (ESI)

Higher sensitivity is achieved at lower flow rates due to increased analyte ionization efficiency (Gale et al (1993) Rapid Commun. Mass Spectrom. 7:1017). Thus by performing electrospray injection of a sample-containing fluid at flow rates in the nanoliter per minute range provides for accurate quantitation after proper calibration, and the high sensitivity for an analyte contained within the fluid when combined with mass spectrometry. Systems and devices including a miniaturized and consolidated micro-column and micro-column array having affinity chromatographic adsorbents, which offer high selectivity and sensitivity, and accurate qualitative analysis as front ends to MS have been reported (U.S. Pat. No. 6,811,689; U.S. Pat. No. 6,020,208; U.S. Pat. No. 6,579,719).

Masses of relatively high molecular weight compounds such as antibodies can be detected at mass-to-charge ratios (m/z) that are easily determined by most mass spectrometers (typical m/z ranges of up to 2000 to 3000). Electrospray ionization mass spectrometry ESI-MS, in particular, is suited for charged, polar or basic compounds and for analyzing multiply charged compounds with excellent detection limits. ESI thus allows detection and characterization of large biomolecules, such as antibodies and antibody-drug conjugates with molecular weight (MW) of 150,000 or higher. With high-mass ions, a series of multiply charged molecular ions are typically observed. The molecular weight for positive ions is determined by multiplying the measured m/z ratio with the number of charges (n) minus the mass of the cation (C+) times the number of charges (n) on that ion.

The ESI method allows the presence or absence of fragmentation to be controlled by controlling the interface lens potentials. Electrospray ionization (ESI) is compatible with liquid separation methods (front end), as well as mass spectrometric detection methods (back end) ("Electrospray Ionization Mass Spectrometry: Fundamentals, Instrumentation, and Applications", Cole, R. B., Ed. (1997) Wiley, New York.

ESI-MS data may be acquired by averaging a number of scans together and smoothing the data to provide good peak intensity and shape. For low-mass compounds, the most abundant peaks observed are often the [M+H]+ ions in the positive-ion mode and [M−H]— in the negative ion mode. Doubly and triply charged ions as well as dimers may also be observed. Doubly charged positive ions will be observed at a mass (MW+2C+)/2 where MW is the molecular weight and C+ is the ionizing cation, such as $H^+$, $Na^+$, or $NH4^+$. Except for the very low mass compounds, the detected ions will be multiply charged. Due to the soft (low ionizing potential) conditions of ESI, typically only molecular ions are observed. ESI spectra may have several molecular ion peaks that differ in the mass to charge ratio due to various numbers of charges the ion possesses.

A dilute solution of a sample, e.g. ADC or other biomolecule may be slowly pumped through a hypodermic needle for ESI-MS analysis. The sample may be introduced via flow injection or LC/MS. Typical flow rates range from less than 1 microliter (µl) per minute up to about one milliliter (ml) per minute. ESI is particularly suited for large biological molecules that are otherwise difficult to vaporize or ionize. The needle is held at a high voltage and the strong electric field at the end of the needle charges the nebulized solution and creates charged droplets. The charged droplets evaporate water to ultimately yield molecular ions that travel into the vacuum chamber through a small orifice. During the process of solvent evaporation, the non-covalently bound complex is transferred from solution to gas phase. (Hu et al (1994)). Gentle desolvation conditions are generally required to maintain the intact gas-phase complex. The orifice may be heated to ensure that the ions are completely desolvated. Some MS systems may employ a counter-flowed heated gas. Charged droplets are emitted from a hypodermic needle and shrink as they evaporate solvent before entering a vacuum chamber. Heat and gas flows may be used to aid desolvation. The amount of sample required for ESI measurements may be reduced by reducing the fluid flow by use of small capillary electrospray emitter, tips, a process known as nanoelectrospray. Nanoelectrospray methods can produce a constant signal for about 10-30 minutes for a 1 µl sample. The low flow has been shown to increase the ion efficiency and reduce ion suppression. Nanoelectrospray methods are frequently used for MS/MS protein studies (Korner et al (1996) J. Am. Soc. Mass Spectrom. 7:150-156; Mann, M. and Wilm, M. (1996) Anal. Chem. 68:1-8.

ESI of proteins produce multiply charged ions with the number of charges tending to increase as the molecular weight increases. The number of charges on a given ionic species may be determined by methods such as: (i) comparing two charge states that differ by one charge and solving simultaneous equations; (ii) looking for species that have the same charge but different adduct masses; and (iii) examining the mass-to-charge ratios for resolved isotopic clusters. The methods of ESI and ESI-MS and parameters needed to conduct these methods are well known in the art. The gentleness of the electrospray ionization process allows intact antibody conjugates to be directly detected by mass spectrometry.

In one embodiment, a Q1 mass spectrum of the protein, antibody, antibody fragment or antibody-conjugates (large molecules) is run as part of the method. A suitable quality Q1 mass spectrum of a large molecule can be obtained. Since there is potential for the protein envelope to shift, all the solvents used for chromatography are made fresh and acid is added to the elution solvent to position the spectrum envelop in the observed range. For proteins of greater than 100,000 mass units, an acid such as formic acid can be used at about 0.1% (volume) in the elution solvents, for example, both solvent A (water) and B (acetonitrile). A stronger acid can be used, such as trifluoroacetic acid (TFA), at 0.05% (volume) TFA for both A and B solvents for proteins with less than 100,000 mass units. As the amount of formic acid is decreased, the intact glycosylated antibody, trastuzumab, picks up more charge, shifting the envelope further to the left and into the observed range of m/z (1800-3000 m/z). As the declustering potential (DP) voltage is increased from about 30-120V to about 70-190V, the charge on the antibody increases even further. Thus voltage applied, solvent composition, and ion pairing agents are factors to consider and adjust. The declustering potential (DP) may be increased (ramped) to acquire enough resolution to select the best charge ion range. Linearity may be obtained over a wide range of m/z. Deglycosylation of the antibody assists quantitation of intact antibody or heavy chain, fragments or ADC. Glycosylation contributes to lower ionization efficiency and thus reduced sensitivity. When quantitating antibody or antibody fragment conjugates, deglycosylation of the antibody may reduce the heterogeneity of the mass spectrum, increase sensitivity and thus simplifying the analysis.

Deconvolution tables are used to determine the exact mass to charge ratio (m/z) for each species to quantitated. Deconvolution software applications such as Analyst™ QS (Applied Biosystems, Foster City, Calif.) are commercially available and/or provided with mass spectrometers. Deconvolution software generally provides the user with a table of deconvoluted masses as well as a sub-table of m/z ions used to calculate these masses.

E. Kits

As a matter of convenience, the assay methods of this invention can be provided in the form of a kit. Such a kit is a packaged combination including the basic elements of:

(a) a capture reagent comprised of an anti-idiotypic antibody against the antibody of interest;

(b) a detectable (labeled or unlabeled) antibody that binds to the antibody of interest; and (c) instructions on how to perform the assay method using these reagents. These basic elements are defined hereinabove.

The kit may further comprise a solid support for the capture reagents, which may be provided as a separate element or on which the capture reagents are already immobilized. Hence, the capture antibodies in the kit may be immobilized on a solid support, or they may be immobilized on such support that is included with the kit or provided separately from the kit. In some embodiments, the capture reagents are coated on a microtiter plate. The detectable antibodies may be labeled antibodies detected directly or unlabeled antibodies that are detected by labeled antibodies directed against the unlabeled antibodies raised in a different species. Where the label is an enzyme, the kit will ordinarily include substrates and cofactors required by the enzyme; where the label is a fluorophore, a dye precursor that provides the detectable chromophore; and where the label is biotin, an avidin such as avidin, streptavidin, or streptavidin conjugated to HRP or 0-galactosidase with MUG.

In various embodiments, the anti-idiotypic antibody is one or more of any of the anti-idiotypic antibodies disclosed herein. In some embodiments, the anti-idiotypic antibody is selected from (a) a first anti-idiotypic antibody comprising the heavy chain sequence of SEQ ID NO: 5 and the light chain sequence of SEQ ID NO: 7; (b) a second anti-idiotypic antibody comprising a heavy chain sequence of SEQ ID NO: 9 and a light chain sequence of SEQ ID NO: 11; and (c) a combination thereof.

The kit also typically contains the antibody of interest as a standard (e.g., purified anti-CI and/or anti-gH), as well as other additives such as stabilizers, washing and incubation buffers, and the like.

The components of the kit will be provided in predetermined ratios, with the relative amounts of the various reagents suitably varied to provide for concentrations in solution of the reagents that substantially maximize the sensitivity of the assay. Particularly, the reagents may be provided as dry powders, usually lyophilized, including excipients, which on dissolution will provide for a reagent solution having the appropriate concentration for combining with the sample to be tested.

III. Examples

The following are examples of methods and compositions of the invention. It is understood that various other embodiments may be practiced, given the general description provided above.

Example 1

Generation of Anti Anti-CI and Anti-gH Hybridomas

Five Balb/c mice (Charles River Laboratories International, Inc., Wilmington, Mass., USA) were hyperimmunized, in each hind footpad and intraperitoneally at 3-4 day intervals, with anti-CI or anti-gH in an adjuvant containing metabolizable squalene, Tween 80, trehalose 6,6-dimycolate and monophosphoryl lipid A (all components obtained from Sigma Aldrich, USA). After 4 to 6 boosts, serum titers were evaluated by standard enzyme-linked immunosorbant assay (ELISA) to identify mice with positive serum titers to anti-CI or anti-gH. B cells from spleens and popliteal lymph nodes were fused with mouse myeloma cells (X63.Ag8.653 or P3X63Ag.U1; American Type Culture Collection, Manassas, Va., USA) by electrofusion (Hybrimune-Hybridoma Production System; Harvard Apparatus, Inc., Holliston, Mass., USA). After 10-14 days, hybridoma supernatants were harvested and screened for CDR specific antibody production by ELISA. All specific clones were then re-screened in a preliminary HCMV PK ELISA, in which candidate anti-ID materials were used as reagents to coat ELISA plates and capture anti-CI and anti-gH, and polyclonal anti-human antibodies were used as detection reagents. Hybridoma clones 1.9E1.1, 4.25B10.15 and 2.41A2.4 showed high specific binding in the preliminary HCMV PK ELISAs after the first round of single cell per well subcloning (FACSAria cell sorter; BD Biosciences, San Jose, Calif., USA), and therefore were scaled up (Innova 2000 Shake Flask Format; New Brunswick Scientific, Enfield, Conn., USA) for antibody production. The binding pattern of clone 2.41A2.4 in the PK assay suggested that this clone binds an epitope inclusive of the lambda light chain framework. Supernatants were purified by affinity chromatography (MabSelect SuRe; GE Healthcare Bio-Sciences, Piscataway, N.J., USA), sterile-filtered, and stored at 4° C. in PBS. Isotypes of the monoclonal antibodies were determined using the Isostrip Mouse mAb Isotyping Kit (Roche Applied Biosciences, Indianapolis, Ind., USA). The isotypes were determined to be IgG1, lambda (1.9E1.1), IgG1, kappa (4.25B10.15) and IgG2a, kappa (2.41A2.4).

The binding affinities of the monoclonal antibodies were determined by Biacore analysis, as shown in Table 2.

TABLE 2

| Monoclonal Antibody | Antibody Bound | Binding Affinity |
|---|---|---|
| 4.25B10.15 | Anti-CI | 4.7 nM |
| 2.41A2.4 | Anti-CI | 17 nM |
| 1.9E1.1 | Anti-gH | 0.1 nM |

The amino acid sequences of the heavy and light chain variable domains for monoclonal antibodies 4.25B10.15 and 1.9E1.1 were determined, as shown in FIGS. 1 and 2 for 4.25B10.15, and in FIGS. 3 and 4 for 1.9E1.1.

The hypervariable regions of the heavy chain of monoclonal antibody 4.25B10.15 as shown in FIG. 1 are:

```
                                           SEQ ID NO: 13
    HVR-H1 NYLIE

SEQ ID NO: 14
    HVR-H2 VINPGSGGTNYNEKFEA

SEQ ID NO: 15
    HVR-H3 HGSSYWYFDV
```

The hypervariable regions of the light chain of monoclonal antibody 4.25B10.15 as shown in FIG. 2 are:

```
                                           SEQ ID NO: 16
    HVR-L1 RASQSISDYLH

SEQ ID NO: 17
    HVR-L2 YASQSIS

SEQ ID NO: 18
    HVR-L3 QNGHSFPYT
```

The hypervariable regions of the heavy chain of monoclonal antibody 1.9E1.1 as shown in FIG. 3 are:

```
                                           SEQ ID NO: 19
    HVR-H1 DYWMY

SEQ ID NO: 20
    HVR-H2 AIDTSDSYTTYNQNFKG

SEQ ID NO: 21
    HVR-H3 SGFPLFYYPMDY
```

The hypervariable regions of the light chain of monoclonal antibody 1.9E1.1 as shown in FIG. 4 are:

```
                                           SEQ ID NO: 22
    HVR-L1 RSSTGAVTTSNYAN

SEQ ID NO: 23
    HVR-L2 GTVNRAP

SEQ ID NO: 24
    HVR-L3 ALWYSNHLV
```

Example 2

ELISA Assay for Detection of Anti-gH

FIG. 5 shows a schematic diagram of an ELISA assay used for detection of anti-gH (referred to as the "anti-gH clinical PK ELISA"). A biotin-conjugated anti-idiotypic antibody to anti-gH is bound to streptavidin-coated microplates and used to detect anti-gH in the sample. The bound anti-gH is detected using an HRP-conjugated mouse anti-human IgG Fcg antibody.

Biotin-conjugated anti-idiotypic antibody is diluted at 500 ng/mL in assay diluent (PBS/0.5% BSA/0.05% polysorbate 20/0.35 M NaCl/0.25% CHAPS/5 mM EDTA/0.05% ProClin 300, pH 7.4±0.1). Roche SA plates are washed three times before use with wash buffer (PBS/0.05% polysorbate 20, pH7.46) before use. 50 µl/well of biotin-conjugated anti-idiotypic antibodies (1.9E1.1) is added to streptavidin-coated plates, and the plates are incubated for 25-35 minutes at room temperature with agitation. The curve standards, assay controls or samples are diluted 1:50 in assay diluent (described above). The diluted samples, curve standards and assay controls are added to the plates and incubated for 100-130 minutes at room temperature with agitation. The plates are washed four times. 100 µl/well of HRP— conjugated mouse anti-huIgG Fcγ (8 ng/ml) is added, and the plates incubated for 1 hr±5 minutes at room temperature with shaking. The plates are washed four times, and 100 µl/well of TMB is added. The plates are incubated for 10-15 minutes at room temperature with agitation. 100 µl of 1 M phosphoric acid is added to each well. The plates are read using a 450 nm read wavelength and a 620 or 630 nm reference wavelength.

Figure 6:
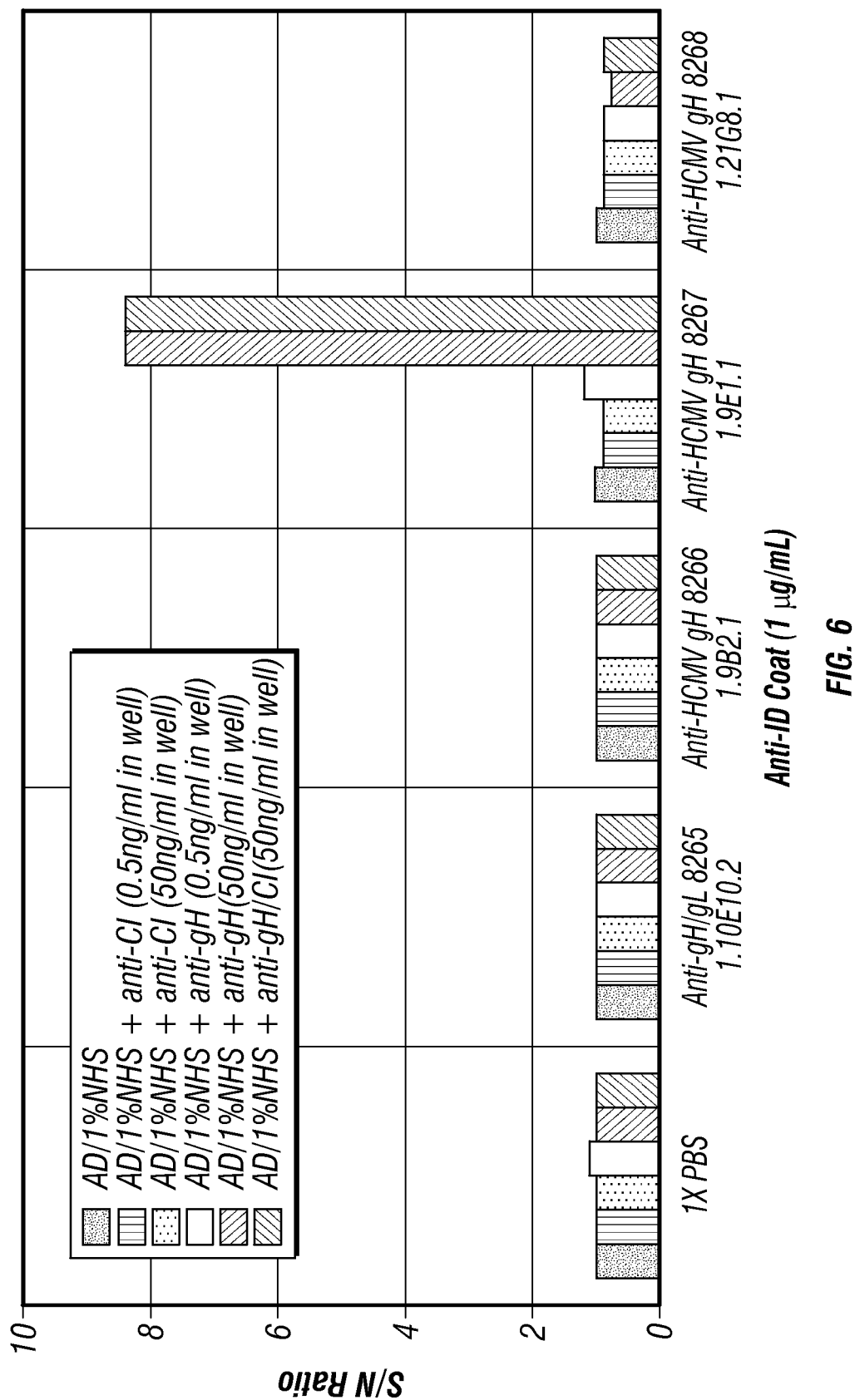
FIG. 6 shows the binding activity of various purified anti-idiotypic antibodies to the anti-HCMV antibodies anti-CI and anti-gH as determined using the anti-HCMV PK ELISA described in Example 2.

FIG. 6 shows the binding activity of various anti-idiotypic antibodies to anti-CI and anti-gH as tested in the preliminary anti-HCMV human PK ELISA. The assay was carried out as follows: microtiter ELISA plates were coated with anti-idiotypic monoclonal antibodies at 1 µg/mL in PBS overnight. Anti-CI and anti-gH were diluted in 1% NHS and added to the wells, being subsequently detected with 50 ng/mL (in-well concentration) of HRP-Sheep anti-huIgG.

As shown in FIG. 6, only one anti-idiotypic antibody, 1.9E1.1, gave an optical density (OD) in the presence of anti-gH that was greater than two-fold the OD in the absence of anti-gH. The other anti-idiotypic antibodies gave high background OD, suggesting cross-reaction of those anti-idiotypic antibodies with endogenous IgG in human serum (NHS).

Figure 7:
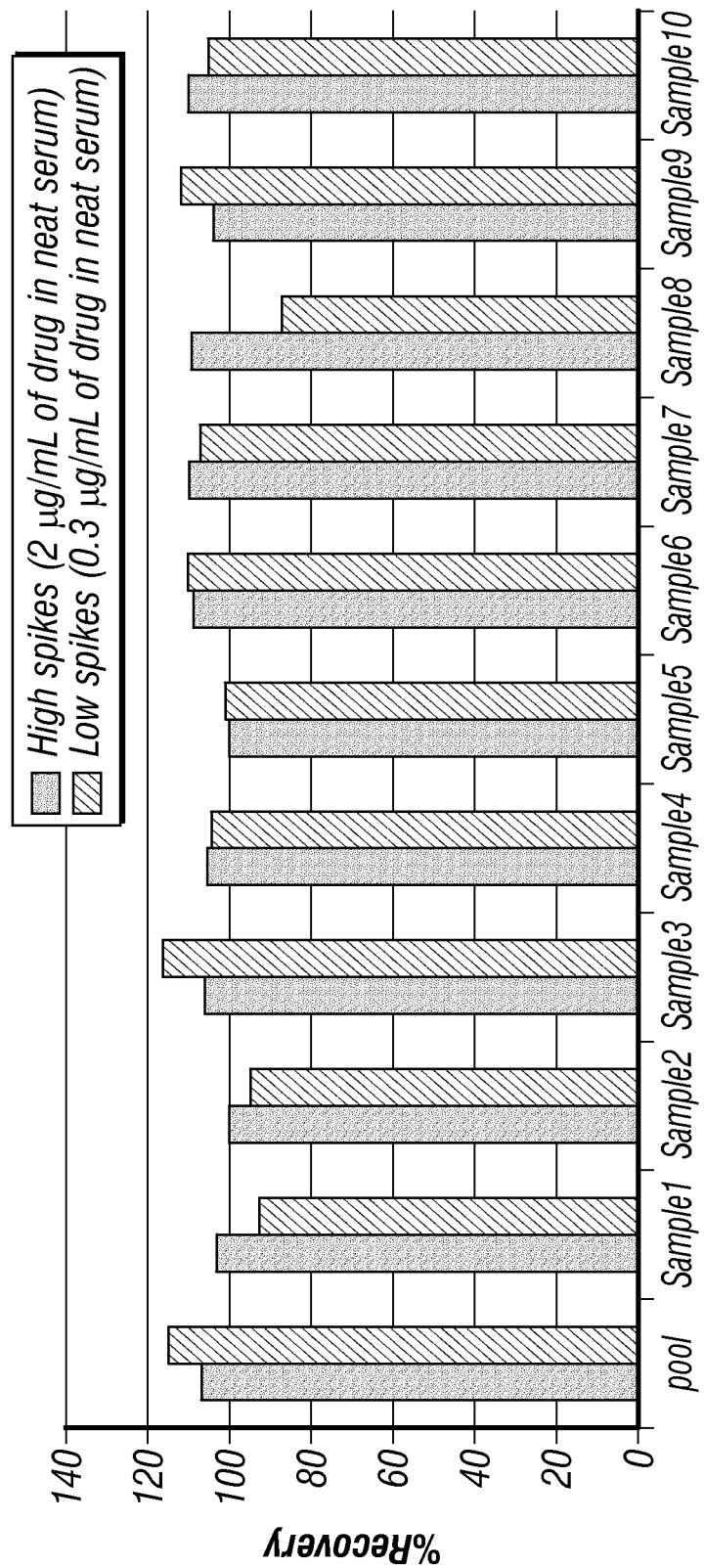
FIG. 7 shows the recovery of individual serum samples spiked with the anti-HCMV antibody anti-gH using anti-idiotypic monoclonal antibody 1.9E1.1 as the capture antibody in the anti-HCMV PK ELISA assay described in Example 2.

The anti-gH clinical PK ELISA was used to quantify the amount of anti-gH spiked into sera from individual donors. Anti-gH was spiked at either high (2 µg/mL) or low (0.3 µg/mL) concentrations in neat serum. FIG. 7 shows the percent recovery of individual serum spikes with anti-gH using 1.9E1.1 as the capture antibody. The assay showed that anti-idiotypic antibody 1.9E1.1 provided good accuracy with all individual sera, spiked at both low and high anti-gH concentrations.

Example 3

ELISA Assay for Detection of Anti-CI

Figure 8:
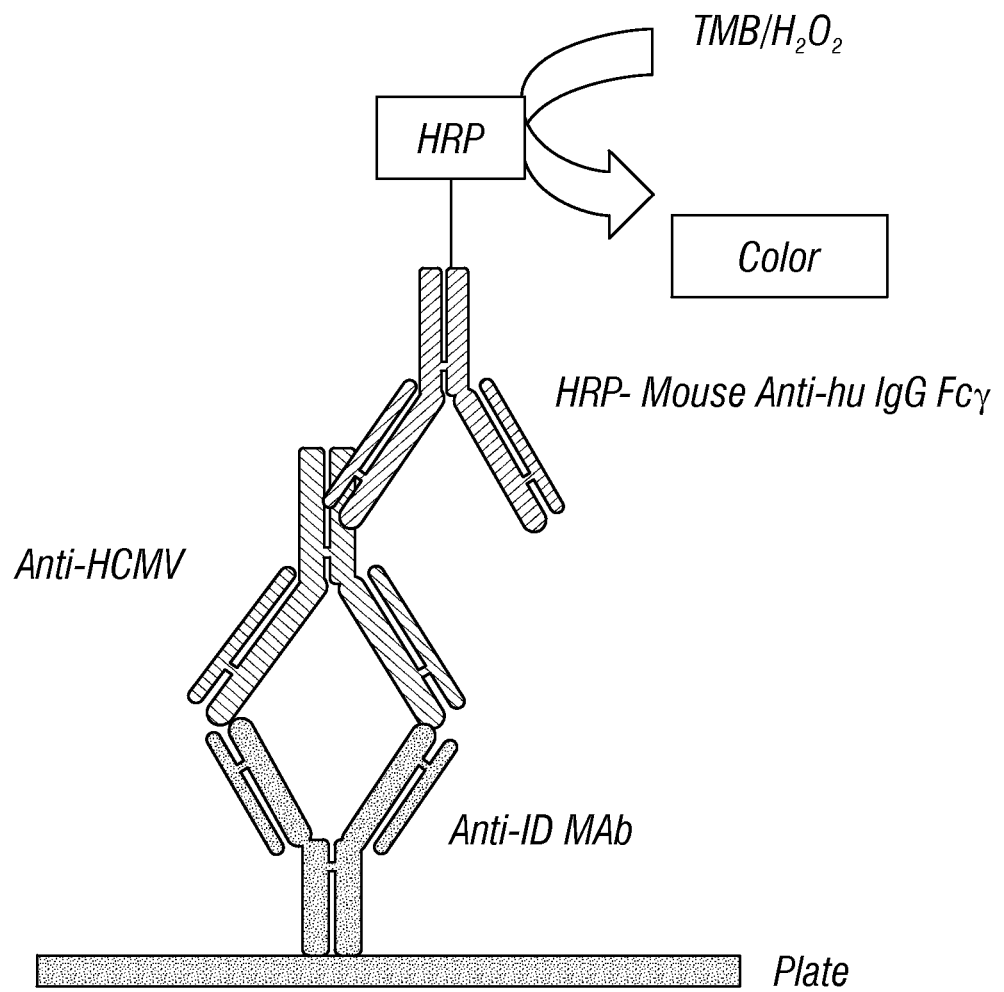
FIG. 8 shows an anti-HCMV PK ELISA format whereby an anti-HCMV idiotypic antibody (e.g. 4.25B10.15) is immobilized on a solid support for binding to a therapeutic anti-HCMV antibody. The complex is then bound by a mouse anti-human IgG Fcγ antibody conjugated to HRP for chemiluminescent detection.

FIG. 8 is a schematic diagram of an ELISA assay used for detection of anti-CI (referred to as the "anti-CI clinical PK ELISA"). Anti-idiotypic antibody to anti-CI is bound to microplates and used to detect anti-CI in the sample. The bound anti-CI is detected using an HRP-conjugated mouse anti-human IgG Fcg antibody.

Microtiter plates are coated overnight at 2-8° C. with 100 µl per well of 0.75 µg/ml anti-CI idiotypic antibody (in 0.05 M sodium carbonate buffer, pH9.6±0.1). The plates are washed three times with 400 µl per well per cycle of wash buffer. 200 µl per well of blocking buffer (PBS/0.5% BSA/0.05% polysorbate 20/0.05% ProClin 300, pH 7.4±0.1) is added, and the plates are incubated at room temperature with shaking for 1-3 hours. Standard curves are prepared with standard/sample diluent (assay diluent with 0.5% normal pooled human serum; assay diluent is composed of PBS/0.5% BSA/0.05% polysorbate-20/0.35 M NaCl/0.25% CHAPS/5 mM EDTA/ 0.05% ProClin 300, pH 7.4±0.1). The plates are washed three times with 400 µl per well per cycle of wash buffer. Diluted standards, controls and samples are added to plates at 100 µl per well, in duplicate. The plates are incubated at room temperature with shaking for 2 hours±10 minutes. The plates are washed four times with 400 µl per well per cycle of wash buffer. HRP conjugates diluted in conjugate buffer (PBS/ 0.5% BSA/0.05% polysorbate 20/0.05% ProClin 300, pH 7.4±0.1) are added at 100 µl per well. The plates are incubated at room temperature with shaking for 1 hour±5 minutes, following which the plates are washed four times with 400 µl per well per cycle of wash buffer. 100 µl per well of TMB substrate is added, and the plates are incubated for approximately 15 minutes at room temperature with shaking 100 µl of 1 M phosphoric acid is added to each well. The plates are read using a 450 nm read wavelength and a 620 or 630 nm reference wavelength.

The anti-CI clinical PK ELISA assay was carried out using plates coated with varying concentrations of capture antibody 4.25B10.15 in order to optimize the coating concentration. As shown in Table 3, plates coated with 0.75 mg/ml of antibody 4.25B10.15 gave the optimum signal to background ratio. Background (bkgd) equals the assay signal obtained with unspiked human serum.

TABLE 3

| | Plate coat with 4.25B10.15 (73427-34) | | | | | |
|---|---|---|---|---|---|---|
| 8G8 (µg/mL) | coat 1 µg/mL | Signal/bkgd ratio | coat 0.75 µg/mL | Signal/bkgd ratio | coat 0.5 µg/mL | Signal/bkgd ratio |
| 16 | 1.876 | 13.8 | 1.593 | 19.1 | 1.281 | 14.7 |
| 8 | 1.771 | 13.0 | 1.378 | 16.5 | 1.075 | 12.3 |
| 4 | 1.371 | 10.0 | 1.107 | 13.3 | 0.901 | 10.4 |
| 1 | 0.599 | 4.4 | 0.439 | 5.3 | 0.379 | 4.3 |
| 0.5 | 0.372 | 2.7 | 0.271 | 3.2 | 0.231 | 2.7 |
| 0.25 | 0.254 | 1.9 | 0.174 | 2.1 | 0.161 | 1.8 |
| 0.125 | 0.194 | 1.4 | 0.128 | 1.5 | 0.120 | 1.4 |
| bkgd | 0.136 | | 0.084 | | 0.087 | |

The anti-CI clinical PK ELISA was run with a standard curve using anti-CI at varying concentrations spiked into 0.5% human serum pool. Results are summarized in Table 4. The assay showed a consistent dose response, and increasingly higher signal to background (S/B) ratio with increasing concentrations of anti-CI.

TABLE 4

| Anti-CI ug/mL | OD | S/B ratio |
|---|---|---|
| 20 | 1.970 | 22.3 |
| 10 | 1.725 | 19.6 |
| 5 | 1.203 | 13.6 |
| 2.5 | 0.743 | 8.4 |
| 1.25 | 0.431 | 4.9 |
| 0.625 | 0.261 | 3.0 |
| 0.313 | 0.174 | 2.0 |
| 0.156 | 0.134 | 1.5 |
| bkgd | 0.088 | |

Figure 9:
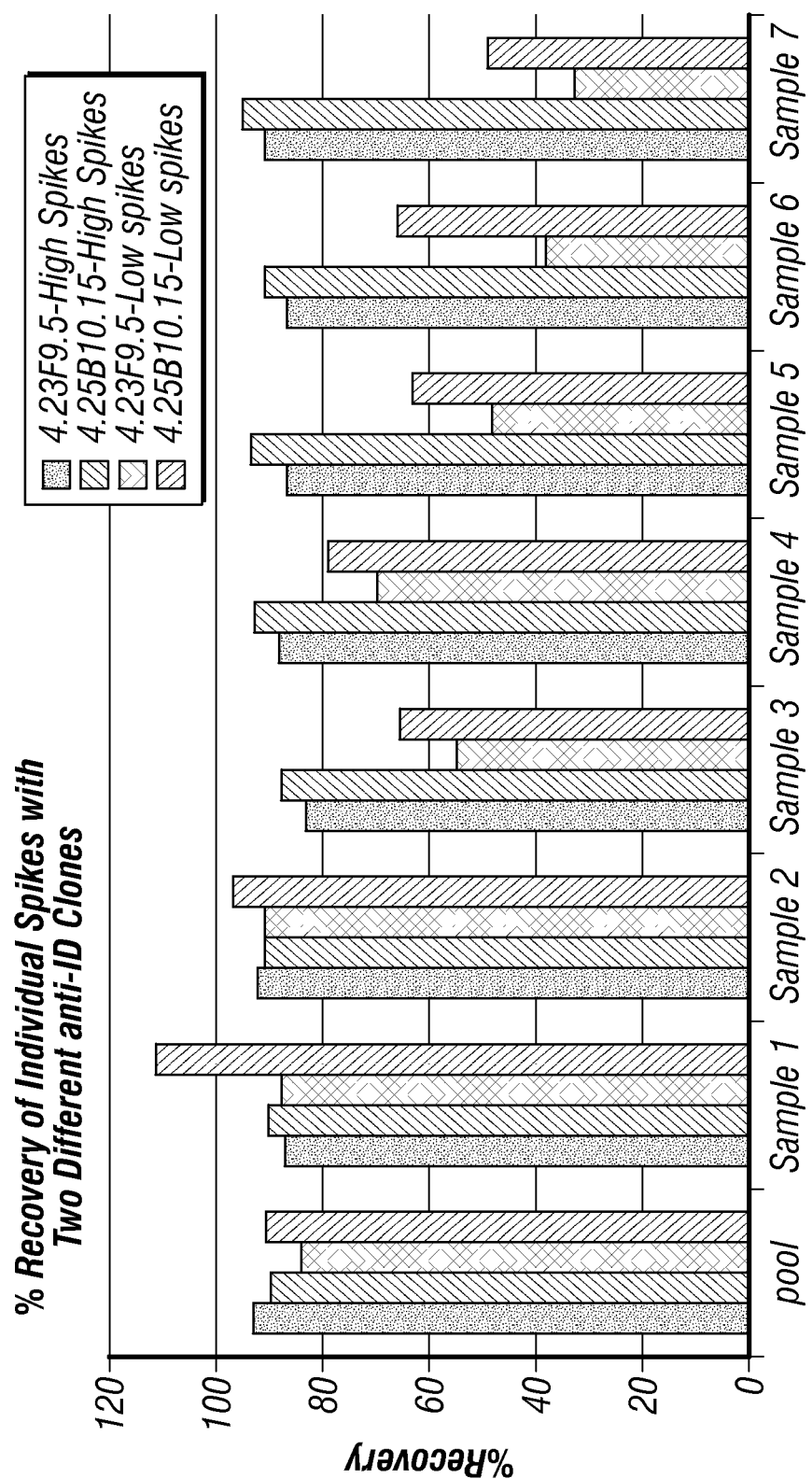
FIG. 9 shows the recovery of individual serum samples spiked with the anti-HCMV antibody anti-CI using anti-idiotypic monoclonal antibody 4.25B10.15 or 4.23F9.5 as the capture antibody in the anti-HCMV PK ELISA described in Example 3. Anti-CI was spiked at either at 4 µg/mL (high) or 0.5 µg/mL (low) for the pool sample and samples 1-4; at either 2 µg/mL (high) or 0.6 µg/mL (low) for sample 5, and at either 7.62 µg/mL (high) or 0.476 µg/mL (low) for samples 6 and 7.

The anti-CI clinical PK ELISA was used to quantify the amount of anti-CI spiked into sera from individual donors, using anti-idiotypic antibody 4.25B10.15 or 4.23F9.5 as the capture antibody. Anti-CI was spiked at either at 4 µg/mL (high) or 0.5 µg/mL (low) for the pool sample and samples 1-4; at either 12 µg/mL (high) or 0.6 µg/mL (low) for sample 5, and at either 7.62 µg/mL (high) or 0.476 µg/mL (low) for samples 6 and 7. As shown in FIG. 9, anti-idiotypic antibody 4.25B10.15 performed better than 4.23F9.5, providing accurate spike recovery for all samples, at both high and low anti-CI concentrations.

Example 4

LC-MS/MS Assay for Quantification of Anti-CI and Anti-gH in Human Serum

An LC-MS/MS Assay was developed for quantification of anti-CI and anti-gH in human serum. The assay used immunoaffinity capture to isolate two monoclonal antibodies, anti-CI and anti-gH, from human serum. Characteristic peptide fragments were then produced by proteolysis of the bound antibodies with trypsin, and the chosen signature peptides, along with their stable isotope-labeled internal standards (SIL ISs) were measured as surrogate analytes for anti-CI and anti-gH using HPLC with MS/MS detection. The signature tryptic peptides for anti-CI and anti-gH were as shown:

```
Anti-CI (P2)
                                (SEQ ID NO: 25)
EQFVYVFGGGTK

Anti-CI (P4)
                                (SEQ ID NO: 26)
DTSTSTAYLELSSLR

Anti-gH (P2)
                                (SEQ ID NO: 27)
GLEWVSSINSNSR

Anti-gH (P5)
                                (SEQ ID NO: 28)
LSC*AASGFTFSPYSVFWVR
*Alkylated cysteine residue
```

The SIL ISs comprised stable isotope-labeled amino acids at the amino acid positions shown in bold:

```
Anti-CI (P2)
                                (SEQ ID NO: 25)
EQFVYVFGGGTK

Anti-CI (P4)
                                (SEQ ID NO: 26)
DTSTSTAYLELSSLR

Anti-gH (P2)
                                (SEQ ID NO: 27)
GLEWVSSINSNSR

Anti-gH (P5)
                                (SEQ ID NO: 28)
LSC*AASGFTFSPYSVFWVR
*Alkylated cysteine residue
```

Signature peptides Anti-CI (P2) and Anti-gH (P2) are the primary surrogate peptides used for quantification of anti-CI and anti-gH, respectively, while Anti-CI (P4) and Anti-gH (P5) were secondary surrogate peptides used for quality control purposes. The method is applicable to the quantitation of anti-CI and anti-gH within a nominal range of 0.100 to 20.0 µg/mL. A 25-µL human serum aliquot is sufficient for analysis. Samples are stored in polypropylene tubes and kept frozen at approximately −70° C. prior to analysis.

The following sample types were extracted for evaluation purposes. Except where noted, the anti-idiotypic monoclonal antibody (anti-ID mAb) loads were 3.0 µg each per sample:

Pooled blank (MB) human serum.

Calibration Standards (CALs) fortified with anti-CI and anti-gH (combined) at the following concentrations for each antibody: 0.100, 0.200, 0.400, 1.00, 4.00, 8.00, 10.0 and 20.0 µg/mL (n=2 each level).

Quality Controls (QCs) fortified with anti-CI and anti-gH (combined) at the following concentrations for each antibody: 0.250, 2.00, 7.50 µg/mL (n=4 each level).

Carryover blanks (CB) following high calibrators.

Over the curve dilution QC (DIL QC) prepared at anti-CI and anti-gH concentration of 40 µg/mL and diluted 10-fold prior to aliquoting.

Specificity Samples (SP) from six individual human donors (n=1 each).

Fortified specificity samples (SPF's) from six individual human donors fortified with anti-CI and anti-gH at a concentration of 0.200 µg/mL.

Additional Calibration Standards (CALs) fortified with anti-CI and anti-gH (combined) at the following concentrations: 0.100, 0.200, 0.400, 1.00, 4.00, 8.00, 10.0 and 20.0 µg/mL (n=2 each level) and containing anti-CI anti-ID mAb and anti-gH anti-ID mAb loads of 1.50 µg each per sample.

The samples for analysis were processed by the following steps:

1. Precondition an Immulon 1B 96-well, flat-bottom microtiter plate (Thermo, Product No. 3355) by adding 275 µL of plate-conditioning buffer (0.1:5.0:3.0:0.2:91.7:0.1 Tween 20/Trizma HCl (1 M)/NaCl (5 M)/EDTA (0.5 M)/water/bovine serum albumin, v/v/v/v/w. Gently vortex the plate for approximately 1 min. Discard the conditioning buffer by inverting the plate, and tap plate dry on an absorbent pad.

2. A 25 µL aliquot of serum sample is added to a mixture of 3.0 µg or 1.5 µg anti-CI anti-ID mAb, 3.0 µg or 1.5 µg anti-gH anti-ID mAb and 10 mM HBS-EP buffer (GE Healthcare, Product No. 94318) to yield a total volume of 150 µL in the preconditioned 96-well micro-well plate.

3. Cover the plate with an adhesive film, and incubate at room temperature (RT) for 2 hrs under constant gentle shaking on a titer plate shaker.

4. The required volume of streptavidin Dynabeads M-280 (Life Technologies, Product No. 602-10) (based on 100 µL per well) is buffer exchanged with an equal volume of 10 mM HBS-EP by mixing at RT for 1-2 min. This procedure is repeated thrice. After discarding the supernatant, the volume is made up with 10 mM HBS-EP to 50 µL so that the beads are concentrated 2-fold compared to the initial starting volume.

5. 50 µL of the concentrated beads are then added to each well from step 3 and allowed to bind at RT for 2 hrs under constant gentle shaking 6. Using an external magnet (Biotek 96-well Flat Magnet) and a Biotek plate washer, separate the magnetic beads and discard the unbound proteins in the supernatant. Wash the beads three times with 75 µL of bead washing buffer (5.0:3.0: 0.2:91.8 Trizman HCl (1 M)/NaCl (5 M)/EDTA (0.5 M)/water, v/v/v/v) using the plate washer. Discard the supernatant after the beads are separated using the external magnet. Using the titer plate shaker, shake the titer plate between each of the three washes to resuspend the beads.

7. Wash the beads a fourth time with 200 µL of bead washing buffer, discard the supernatant after the beads are separated using the external magnet, and shake briefly using the titer plate shaker to resuspend.

8. Separate the magnetic beads and discard the supernatant. Wash the beads one time with 75 µL of bead washing solution (20% acetonitrile in water), and shake briefly using the titer plate shaker to resuspend. Separate the magnetic beads and discard the supernatant. Wash the beads a final time with bead washing solution, and shake briefly using the titer plate shaker to resuspend.

9. After the washes are discarded, 75 µL of Rapigest surfactant solution (0.05:40:10 Rapigest (Rapigest SF surfactant, Waters, Product No. 186002122)/Ammonium Bicarbonate, 50 mM/ACN, w/v/v), 25 µL of internal standard (or internal standard diluent i.e. 20% acetonitrile in water), and 10 µL of DTT (0.1 M) is added to each well. The plate is incubated at 60° C. in a preheated oven for ~1 hour.

10. Add 25 µL of iodoacetmide (0.1M) to each well. Mix well. Incubate at RT for ~0.5 hours (protected from light).

11. Add 2.5 µg of trypsin to each well. Mix well. Incubate at 37° C. overnight (16-20 hrs).

12. Add 15 µL of 2M HCl to each well. Mix well. Incubate at 37° C. for ~0.5 hours.

13. Place the plate on a magnet and transfer the entire solution to a Multicreen HTS Filter Plate (Millipore, Part#MSHVN4550) placed on top of a 96-well Eppendorf Lo-bind collection plate.

14. Centrifuge the filter plate/collection plate combination for 5 min at 3000 rpm to collect the filtrate.

15. Seal the plate with an injection mat, and directly inject 15 µL (on a 10 µL injection loop) on the LC/MS/MS system.

Data Reduction

The data system was configured to calculate and annotate the areas of MCMV3068A, MCMV5322A, and internal standard peaks automatically. A calibration curve was constructed using peak area ratios (PARs) of the calibration standards by applying a quadratic, 1/concentration squared weighted, least-squares regression algorithm. All concentrations were then calculated from their PARs against the calibration line.

Initial experiments demonstrated that it was feasible to extend the calibration range of both analytes anti-CI and anti-gH from 0.100 to 20.0 µg/mL for all signature peptides. A quadratic regression ($1/x^2$ weighted) was applied for anti-CI and anti-gH (with a 1.5 µg each anti-ID mAb load).

In addition, assay specificity was tested in multiple individual serum lots, and quality control (QC) samples were prepared and quantified against calibration standards. Good accuracy and precision data was obtained for the QCs for all four signature peptides. Over-the-curve dilution QC samples were successfully diluted in the curve range. Consistent area ratios of the primary and the secondary peptides were observed for both analytes. Specificity samples did not indicate any presence of interference at the analyte retention time. Fortified specificity samples did not indicate any significant evidence of lot-to-lot matrix effects.

The assay was further evaluated as follows, using anti-idiotypic antibody loads of 1.5 µg for each anti-idiotypic antibody. Anti-idiotypic antibody 2.41A2.4 was used for detection of anti-CI, and anti-idiotypic antibody 1.9E1.1 was used for detection of anti-gH. Two sets of standard curves with at least eight calibration points ranging from 0.100 to 20.0 µg/mL of anti-CI and anti-gH respectively were run; one curve at the beginning of the sample batch and one at the end. The back-calculated values of the calibration standards were required to be within ±20% of the nominal concentration. If the back-calculated concentration of a standard fell outside the allowed range, that standard was excluded and the regression analysis of the calibration data repeated until all of the remaining values were within the allowed range. For an acceptable calibration curve, there were at least six calibration levels represented and a minimum of 75% of the total calibration standards in the run remaining following exclusions. At least one blank sample of each of the following types was analyzed: (a) reagent blank without internal standard; (b) matrix blank without internal standard; and (c) matrix blank with internal standard.

Lower limit of quantitation (LLOQ), Low, medium and high-level QC samples (n=6) were run to evaluate intra-assay precision and accuracy. As shown in Table 5, for the LLOQ concentration of anti-CI and anti-gH, the intra-assay coefficient of variation was less than 25.0% (acceptance criterion) for the replicate intra-assay determinations, and the mean accuracy was within ±25.0% (acceptance criterion) of the theoretical analyte concentration. For all other concentrations of anti-CI and anti-gH, the intra-assay coefficient of variation was less than 20% for the replicate intra-assay determinations, and the mean accuracy was within ±20.0% of the theoretical analyte concentration. Thus the assay demonstrates acceptable precision and accuracy over a wide range of drug concentrations.

An additional "over the curve" matrix quality control pool was prepared with anti-CI and anti-gH concentration of approximately 600 µg/mL, in order to assess the ability to dilute samples originally above the upper limit of the standard curve. Six replicates of this QC pool were individually diluted 100-fold using two serial 10-fold dilutions, and analyzed. The dilution was prepared using two serial 10-fold dilutions. As shown in Table 6, the intra-assay coefficient of variation was less than 20% for the replicate intra-assay determinations, and the mean accuracy was within ±20.0% of the theoretical analyte concentration.

TABLE 5

| Antibody Run ID | Anti-CI | | | | Anti-gH | | | |
| --- | --- | --- | --- | --- | --- | --- | --- | --- |
| | IA-0 | IA-1 | IA-2 | IA-3 | IA-0 | IA-1 | IA-2 | IA-3 |
| | (µg/mL) | | | | (µg/mL) | | | |
| | 0.108 | 0.238 | 1.60 | 16.8 | 0.0989 | 0.232 | 1.64 | 15.8 |
| | 0.124 | 0.227 | 1.65 | 17.3 | 0.109 | 0.229 | 1.44 | 13.3 |
| | 0.105 | 0.221 | 1.70 | 15.7 | 0.120 | 0.210 | 1.70 | 14.9 |
| | 0.109 | 0.222 | 1.66 | 16.4 | 0.108 | 0.225 | 1.75 | 13.3 |
| | 0.103 | 0.192 | 1.62 | 14.6 | 0.111 | 0.225 | 1.26 | 13.4 |
| | 0.105 | 0.211 | 1.72 | 16.1 | 0.116 | 0.217 | 1.50 | 15.5 |
| N | 6 | 6 | 6 | 6 | 6 | 6 | 6 | 6 |
| Theoretical Concentration | 0.100 | 0.200 | 1.50 | 15.0 | 0.100 | 0.200 | 1.50 | 15.0 |
| Mean | 0.109 | 0.219 | 1.66 | 16.1 | 0.111 | 0.223 | 1.55 | 14.4 |
| S.D. | 0.0078 | 0.0157 | 0.047 | 0.930 | 0.0073 | 0.0082 | 0.185 | 1.17 |
| % C.V. | 7.18 | 7.17 | 2.85 | 5.76 | 6.55 | 3.67 | 11.9 | 8.16 |
| % Difference from theoretical | 9.02 | 9.30 | 10.5 | 7.66 | 10.7 | 11.5 | 3.20 | −4.18 |

TABLE 5-continued

| Antibody Run ID | Anti-CI | | | | Anti-gH | | | |
|---|---|---|---|---|---|---|---|---|
| | IA-0 | IA-1 | IA-2 | IA-3 | IA-0 | IA-1 | IA-2 | IA-3 |
| | (µg/mL) | | | | (µg/mL) | | | |
| Low Limit | 0.0750 | 0.160 | 1.20 | 12.0 | 0.0750 | 0.160 | 1.20 | 12.0 |
| High Limit | 0.125 | 0.240 | 1.80 | 18.0 | 0.125 | 0.240 | 1.80 | 18.0 |

TABLE 6

| | Antibody | |
|---|---|---|
| Run ID | Anti-CI QC 4 (µg/mL) | Anti-gH QC 4 (µg/mL) |
| | 676 | 559 |
| | 682 | 635 |
| | 595 | 748 |
| | 598 | 720 |
| | 649 | 671 |
| | 637 | 650 |
| N | 6 | 6 |
| Theoretical Concentration | 600 | 600 |
| Mean | 639 | 664 |
| S.D. | 37.4 | 66.7 |
| % C.V. | 5.85 | 10.1 |
| % Difference from theoretical | 6.56 | 10.6 |
| Low Limit | 480 | 480 |
| High Limit | 720 | 720 |

Matrix samples from at least ten different individual lots/donors (both unfortified (SP) and fortified with internal standard (SP/IS) only) were analyzed to evaluate assay specificity. For the unfortified specificity samples, the response of any interfering chromatographic background peak present at the expected retention time of an internal standard was less than 5% of the mean chromatographic response determined for that internal standard in the specificity samples fortified with that internal standard. For the specificity samples fortified with internal standard(s) only, the response ratio (interfering background peak response/internal standard peak response) measured in these samples was less than 20% of the mean response ratio determined for the corresponding analyte in the acceptable lower limit of quantification (LLOQ) CALs and QCs analyzed during the run, demonstrating acceptable assay specificity for both anti-CI and anti-gH.

Assay selectivity was evaluated by analysis of ten different individual lots fortified with the target analyte(s) at the low QC level and internal standard(s) at the level of use. These test samples are identified as SPF. The intra-assay coefficient of variation was less than 20% for the replicate determinations, and the mean accuracy was within ±20.0% of the theoretical analyte concentration for all test samples of anti-CI (Table 7) and for 9/10 test samples of anti-gH (Table 8), confirming acceptable assay selectivity for both antibodies.

TABLE 7

| Sample ID | SPF 1 | SPF 2 | SPF 3 | SPF 4 | SPF 5 | SPF 6 | SPF 7 | SPF 8 | SPF 9 | SPF 10 |
|---|---|---|---|---|---|---|---|---|---|---|
| | 0.189 | 0.157 | 0.215 | 0.182 | 0.184 | 0.182 | 0.167 | 0.178 | 0.218 | 0.186 |
| | 0.171 | 0.193 | 0.204 | 0.183 | 0.224 | 0.182 | 0.178 | 0.166 | 0.185 | 0.194 |
| | 0.211 | 0.217 | 0.228 | 0.192 | 0.150 | 0.204 | 0.220 | 0.186 | 0.190 | 0.202 |
| N | 3 | 3 | 3 | 3 | 3 | 3 | 3 | 3 | 3 | 3 |
| Theoretical Conc'n | 0.200 | 0.200 | 0.200 | 0.200 | 0.200 | 0.200 | 0.200 | 0.200 | 0.200 | 0.200 |
| Mean | 0.190 | 0.189 | 0.216 | 0.186 | 0.186 | 0.189 | 0.188 | 0.177 | 0.198 | 0.194 |
| S.D. | 0.0199 | 0.0305 | 0.0121 | 0.0052 | 0.0370 | 0.0126 | 0.0278 | 0.0099 | 0.0175 | 0.0079 |
| % C.V. | 10.5 | 16.1 | 5.59 | 2.82 | 19.9 | 6.65 | 14.8 | 6.62 | 8.87 | 4.09 |
| % Difference from theoretical | −4.91 | −5.52 | 7.76 | −7.17 | −7.02 | −5.38 | −5.92 | −11.7 | −1.23 | −2.83 |
| Low Limit | 0.160 | 0.160 | 0.160 | 0.160 | 0.160 | 0.160 | 0.160 | 0.160 | 0.160 | 0.160 |
| High Limit | 0.240 | 0.240 | 0.240 | 0.240 | 0.240 | 0.240 | 0.240 | 0.240 | 0.240 | 0.240 |

TABLE 8

| Sample ID | SPF 1 | SPF 2 | SPF 3 | SPF 4 | SPF 5 | SPF 6 | SPF 7 | SPF 8 | SPF 9 | SPF 10 |
|---|---|---|---|---|---|---|---|---|---|---|
| | 0.201 | 0.152 | 0.221 | 0.161 | 0.213 | 0.191 | 0.191 | 0.157 | 0.179 | 0.201 |
| | 0.189 | 0.265 | 0.217 | 0.230 | 0.202 | 0.199 | 0.185 | 0.172 | 0.187 | 0.238 |
| | 0.156 | 0.193 | 0.175 | 0.219 | 0.175 | 0.225 | 0.193 | 0.249 | 0.204 | 0.204 |
| N | 3 | 3 | 3 | 3 | 3 | 3 | 3 | 3 | 3 | 3 |
| Theoretical Conc'n | 0.200 | 0.200 | 0.200 | 0.200 | 0.200 | 0.200 | 0.200 | 0.200 | 0.200 | 0.200 |
| Mean | 0.182 | 0.204 | 0.205 | 0.204 | 0.196 | 0.205 | 0.190 | 0.193 | 0.190 | 0.214 |
| S.D. | 0.0231 | 0.0572 | 0.0255 | 0.0369 | 0.0194 | 0.0176 | 0.0045 | 0.0495 | 0.0127 | 0.0207 |
| % C.V. | 12.7 | 28.1 | 12.5 | 18.1 | 9.89 | 8.58 | 2.38 | 25.7 | 6.68 | 9.69 |
| % Difference from theoretical | −9.03 | 1.78 | 2.34 | 1.78 | −1.75 | 2.47 | −5.17 | −3.74 | −5.05 | 7.00 |

TABLE 8-continued

| Sample ID | SPF 1 | SPF 2 | SPF 3 | SPF 4 | SPF 5 | SPF 6 | SPF 7 | SPF 8 | SPF 9 | SPF 10 |
|---|---|---|---|---|---|---|---|---|---|---|
| Low Limit | 0.160 | 0.160 | 0.160 | 0.160 | 0.160 | 0.160 | 0.160 | 0.160 | 0.160 | 0.160 |
| High Limit | 0.240 | 0.240 | 0.240 | 0.240 | 0.240 | 0.240 | 0.240 | 0.240 | 0.240 | 0.240 |

A cross-analyte interference check was evaluated for samples fortified with SIL ISs of signature peptides. Cross analyte interference evaluation between same individual analyte signature peptides was not evaluated for samples fortified with anti-CI or anti-gH, since the surrogate signature peptides corresponding to an individual analyte measured in this assay cannot be independently generated using the assay procedure. Rather, cross-analyte interference was evaluated between signature peptides corresponding to anti-CI and signature peptides corresponding to anti-gH. Each internal standard was checked individually for possible contribution of signal to other analytes and internal standards. Control matrix samples ("AI") were fortified with only one internal standard at the expected level of use, and analyzed in triplicate. The contribution to the response of an analyte from a chromatographic peak present at its expected retention time was required to be less than 20% of the mean chromatographic response determined for that analyte in the acceptable LLOQ CALs and/or LLOQ QCs analyzed during the run. The response of an interfering chromatographic background peak present at the expected retention time of an internal standard was required to be less than 5% of the mean chromatographic response determined for that internal standard in the acceptable upper limit of quantitation (ULOQ) CALs and high-level QCs fortified with that internal standard and analyzed during the run. Overall, no significant cross-analyte interferences was observed for sample fortified with SIL ISs of signature peptides of anti-CI and anti-gH.

Cryofreezer freeze/thaw stability was evaluated at low and high QC concentrations by subjecting the QCs to at least three freeze/thaw cycles. At least six replicates were analyzed per level. The coefficient of variation of freeze/thaw samples was less than or equal to 20% for replicate determinations, and the mean accuracy was within ±20% of the theoretical concentration, demonstrating acceptable freeze/thaw stability for both anti-CI and anti-gH.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. An isolated monoclonal anti-idiotypic antibody that specifically binds to an anti-human cytomegalovirus (HCMV) antibody, wherein the anti-HCMV antibody comprises the heavy chain sequence of SEQ ID NO: 1 and the light chain sequence of SEQ ID NO: 2, wherein the isolated monoclonal anti-idiotypic antibody is conjugated to a heterologous moiety or detectable moiety.

2. The isolated monoclonal anti-idiotypic antibody of claim 1, wherein the isolated monoclonal anti-idiotypic antibody comprises three heavy chain hypervariable regions (HVR-H1, HVR-H2 and HVR-H3) and three light chain hypervariable regions (HVR-L1, HVR-L2 and HVR-L3), wherein:
   (a) HVR-H1 comprises the amino acid sequence of SEQ ID NO: 13;
   (b) HVR-H2 comprises the amino acid sequence of SEQ ID NO: 14;
   (c) HVR-H3 comprises the amino acid sequence of SEQ ID NO: 15;
   (d) HVR-L1 comprises the amino acid sequence of SEQ ID NO: 16;
   (e) HVR-L2 comprises the amino acid sequence of SEQ ID NO: 17; and
   (f) HVR-L3 comprises the amino acid sequence of SEQ ID NO: 18.

3. The isolated monoclonal anti-idiotypic antibody of claim 1, wherein the anti-idiotypic antibody comprises the heavy chain sequence of SEQ ID NO: 5 and the light chain sequence of SEQ ID NO: 7.

4. The isolated monoclonal anti-idiotypic antibody of claim 1, wherein the anti-idiotypic antibody specifically binds to at least one HVR of an anti-HCMV antibody comprising the heavy chain sequence of SEQ ID NO: 1 and the light chain sequence of SEQ ID NO: 2.

5. The isolated monoclonal anti-idiotypic antibody of claim 1, wherein the detectable moiety is a detectable label or biotin.

6. An enzyme-linked immunosorbent assay (ELISA) method for specifically detecting in a biological sample the anti-human cytomegalovirus (HCMV) antibody comprising the heavy chain sequence of SEQ ID NO: 1 and the light chain sequence of SEQ ID NO: 2:
   comprising (a) contacting and incubating the biological sample with a capture reagent, wherein the capture reagent is the anti-idiotypic antibody of claim 1, so as to bind the anti-HCMV antibody present in the sample, thereby forming an immunocomplex; and
   (b) contacting the immunocomplex from (a) with a detectable antibody that binds to the anti-HCMV antibody, and measuring the level of the anti-HCMV antibody bound to the anti-idiotypic antibody using a detection means for the detectable antibody.

7. The method of claim 6, wherein the capture reagent is immobilized to a solid support and the method further comprises the step of separating the biological sample from the immobilized capture reagent bound to the anti-HCMV antibody.

8. The method of claim 7, wherein the immobilized capture reagent is conjugated to biotin and bound to a streptavidin coated microtiter plate.

9. The method of claim 6, wherein the detectable antibody is an antibody from a non-human species that binds to human antibodies.

10. The method of claim 9, wherein the detectable antibody is directly detectable, or is conjugated to horseradish peroxidase, or is detected by a fluorometric or calorimetric reagent.

11. The method of claim 6, wherein the isolated monoclonal anti-idiotypic antibody comprises the heavy chain sequence of SEQ ID NO: 5 and the light chain sequence of SEQ ID NO: 7.

12. The method of claim 6, wherein the isolated monoclonal anti-idiotypic antibody comprises three heavy chain hypervariable regions (HVR-H1, HVR-H2 and HVR-H3) and three light chain hypervariable regions (HVR-L1, HVR-L2 and HVR-L3), wherein:
 (a) HVR-H1 comprises the amino acid sequence of SEQ ID NO: 13;
 (b) HVR-H2 comprises the amino acid sequence of SEQ ID NO: 14;
 (c) HVR-H3 comprises the amino acid sequence of SEQ ID NO: 15;
 (d) HVR-L1 comprises the amino acid sequence of SEQ ID NO: 16;
 (e) HVR-L2 comprises the amino acid sequence of SEQ ID NO: 17; and
 (f) HVR-L3 comprises the amino acid sequence of SEQ ID NO: 18.

13. The method of claim 12, wherein the isolated monoclonal anti-idiotypic antibody comprises the heavy chain sequence of SEQ ID NO: 5 and the light chain sequence of SEQ ID NO: 7.

14. The method of claim 6, wherein the biological sample is isolated from a human subject.

15. The method of claim 14, wherein the human subject has been treated with the anti-HCMV antibody comprising the heavy chain sequence of SEQ ID NO: 1 and the light chain sequence of SEQ ID NO: 2.

16. The method of claim 6, wherein the method further comprises using a standard curve to determine the level of the anti-HCMV antibody compared to a known level of the anti-HCMV antibody.

17. The method of claim 6, wherein the biological sample is blood, plasma or serum.

18. An immunoassay kit for specifically detecting in a biological sample the isolated monoclonal anti-human cytomegalovirus (HCMV) antibody comprising the heavy chain sequence of SEQ ID NO: 1 and the light chain sequence of SEQ ID NO: 2; the kit comprising: (a) a container containing, as a capture reagent, at least one isolated monoclonal anti-idiotypic antibody that specifically binds to the antibody of interest; (b) a container containing a detectable antibody that binds to the antibody of interest; and (c) instructions for detecting said antibody of interest;
 wherein the at least one isolated monoclonal anti-idiotypic antibody is conjugated to a heterologous moiety or detectable moiety.

19. The kit of claim 18, wherein the kit is useful in an ELISA method for detecting the antibody of interest.

20. The kit of claim 18, wherein the isolated monoclonal anti-idiotypic antibody is the isolated monoclonal anti-idiotypic antibody comprising the heavy chain sequence of SEQ ID NO: 5 and the light chain sequence of SEQ ID NO: 7.

21. The kit of claim 18, wherein the isolated monoclonal anti-idiotypic antibody comprises three heavy chain hypervariable regions (HVR-H1, HVR-H2 and HVR-H3) and three light chain hypervariable regions (HVR-L1, HVR-L2 and HVR-L3), wherein:
 (a) HVR-H1 comprises the amino acid sequence of SEQ ID NO: 13;
 (b) HVR-H2 comprises the amino acid sequence of SEQ ID NO: 14;
 (c) HVR-H3 comprises the amino acid sequence of SEQ ID NO: 15;
 (d) HVR-L1 comprises the amino acid sequence of SEQ ID NO: 16;
 (e) HVR-L2 comprises the amino acid sequence of SEQ ID NO: 17; and
 (f) HVR-L3 comprises the amino acid sequence of SEQ ID NO: 18.

* * * * *

UNITED STATES PATENT AND TRADEMARK OFFICE
CERTIFICATE OF CORRECTION

| | | |
|---|---|---|
| PATENT NO. | : 9,139,659 B2 | Page 1 of 1 |
| APPLICATION NO. | : 13/841691 | |
| DATED | : September 22, 2015 | |
| INVENTOR(S) | : Hongo et al. | |

It is certified that error appears in the above-identified patent and that said Letters Patent is hereby corrected as shown below:

At (71) on the Title page of the patent:
Please delete "Genetech" and replace with --Genentech--

Signed and Sealed this
Tenth Day of May, 2016

Michelle K. Lee
*Director of the United States Patent and Trademark Office*